(12) United States Patent
Gengrinovitch

(10) Patent No.: US 11,104,698 B2
(45) Date of Patent: Aug. 31, 2021

(54) SALTS OF CONJUGATES FOR CANCER THERAPY

(71) Applicant: BIOSIGHT LTD., Lod (IL)

(72) Inventor: Stela Gengrinovitch, Kfar Hanania (IL)

(73) Assignee: Biosight Ltd., Lod (IL)

( * ) Notice: Subject to any disclaimer, the term of this patent is extended or adjusted under 35 U.S.C. 154(b) by 0 days.

(21) Appl. No.: 15/780,704

(22) PCT Filed: Dec. 1, 2016

(86) PCT No.: PCT/IL2016/051287
§ 371 (c)(1),
(2) Date: Jun. 1, 2018

(87) PCT Pub. No.: WO2017/094011
PCT Pub. Date: Jun. 8, 2017

(65) Prior Publication Data
US 2018/0354982 A1 Dec. 13, 2018

Related U.S. Application Data

(60) Provisional application No. 62/262,428, filed on Dec. 3, 2015, provisional application No. 62/370,257, filed on Aug. 3, 2016.

(30) Foreign Application Priority Data

Jan. 25, 2016 (WO) .................. PCT/IL2016/050077

(51) Int. Cl.
| | | |
|---|---|---|
| *A01N 43/04* | (2006.01) | |
| *A61K 31/70* | (2006.01) | |
| *C07H 19/09* | (2006.01) | |
| *A61K 47/54* | (2017.01) | |
| *C07H 19/06* | (2006.01) | |
| *A61P 35/02* | (2006.01) | |
| *A61P 35/04* | (2006.01) | |

(52) U.S. Cl.
CPC ........... *C07H 19/09* (2013.01); *A61K 47/542* (2017.08); *A61P 35/02* (2018.01); *A61P 35/04* (2018.01); *C07H 19/06* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,296,105 A | 10/1981 | Baurain et al. |
| 4,348,522 A | 9/1982 | Schultz et al. |
| 5,106,951 A | 4/1992 | Morgan, Jr. et al. |
| 5,643,957 A | 7/1997 | Leone-Bay et al. |
| 5,650,386 A | 7/1997 | Leone-Bay et al. |
| 5,962,216 A | 10/1999 | Trouet et al. |
| 6,344,213 B1 | 2/2002 | Leone-Bay et al. |
| 6,428,780 B2 | 8/2002 | Leone-Bay et al. |
| 6,617,306 B2 | 9/2003 | Stein et al. |
| 6,623,731 B2 | 9/2003 | Leone-Bay et al. |
| 7,151,092 B2 * | 12/2006 | Boyer ................. C07F 9/65742 514/110 |
| 7,989,188 B2 | 8/2011 | Gengrinovitch et al. |
| 8,993,278 B2 | 3/2015 | Gengrinovitch et al. |
| 2011/0275590 A1 * | 11/2011 | Gengrinovitch ............ A61K 47/48038 514/49 |
| 2014/0227282 A1 | 8/2014 | Nishitani et al. |
| 2018/0369265 A1 | 12/2018 | Gengrinovitch et al. |

FOREIGN PATENT DOCUMENTS

| | | |
|---|---|---|
| CN | 101812105 A | 8/2010 |
| CN | 101812105 A | 8/2010 |
| JP | H0859688 A | 3/1996 |
| RU | 2085557 C1 | 7/1997 |
| WO | WO/1995/018636 A2 | 7/1995 |
| WO | WO-1995018636 A2 | 7/1995 |
| WO | 96/30036 A1 | 10/1996 |
| WO | 97/36480 A1 | 10/1997 |
| WO | 00/33888 A2 | 6/2000 |
| WO | WO/2002/020715 A2 | 3/2002 |
| WO | 2005/072061 A2 | 8/2005 |
| WO | WO/2006/054310 A1 | 5/2006 |
| WO | WO/2008/072963 A1 | 6/2008 |
| WO | WO/2014/097318 A2 | 3/2015 |

(Continued)

OTHER PUBLICATIONS

Definition of Derivative-Merriam-Webster Online Dictionary, https://www.merriam-webster.com/dictionary/derivative (last visited Apr. 12, 2019).*
Jin et al. J. Kor. Pharm. Sci. (2008), vol. 38, pp. 255-259.*
Fasinu et al. Biopharmaceuticals & Drug Disposition (2011), vol. 32, pp. 185-209.*
Elder, D.P., et al., Use of pharmaceutical salts and cocrystals to address the issue of poor solubility. Int J Pharmaceut (2012), http://dx.doi.org/10.1016/j.ijpharm.2012.11.028.*
Tilborg et al. European Journal of Medicinal Chemistry (2014), vol. 74, pp. 411-426.*
Brynes et al., (1978) Potential antitumor agents via inhibitors of L-asparagine synthetase: Substituted sulfonamides and sulfonyl hydrazides related to glutamine. Journal of pharmaceutical sciences, 67(11), 1550-1553.

(Continued)

*Primary Examiner* — Patrick T Lewis
(74) *Attorney, Agent, or Firm* — Mark S. Cohen; Pearl Cohen Zedek Latzer Baratz LLP

(57) ABSTRACT

Provided relates to pharmaceutically acceptable salts of conjugates including a chemotherapeutic drug and an amino acid or a derivative thereof, which are readily taken up by a target cell and reduce side effects induced by the chemotherapeutic drug. Further, the subject matter relates to pharmaceutically acceptable salts of conjugates comprising cytidine analog drugs and aspartic or glutamic acid and analogs thereof, pharmaceutical compositions including these conjugates and use thereof for the treatment of cancer or a pre-cancer condition or disorder.

22 Claims, 5 Drawing Sheets

(56) References Cited

FOREIGN PATENT DOCUMENTS

| WO | 2015/178265 A1 | 11/2015 |
|---|---|---|
| WO | WO/2017/148129 A1 | 9/2017 |
| WO | WO/2019/012328 A1 | 1/2019 |

OTHER PUBLICATIONS

Brynes et al., (1978) Potential inhibitors of L-asparagine biosynthesis. 4. Substituted sulfonamide and sulfonylhydrazide analogs of L-asparagine. Journal of medicinal chemistry, 21(1), 45-49.

Chhikara et al., (2010) Development of cytarabine prodrugs and delivery systems for leukemia treatment. Expert opinion on drug delivery, 7(12), 44 pages.

Dalal et al., (1986) Arabinofuranosyl-5-azacytosine: antitumor and cytotoxic properties. Cancer research, 46(2), 831-838.

Fong et al., (1988) Possible role of the membrane Na+/H+ antiport in ornithine decarboxylase induction by L-asparagine. Biochemical and biophysical research communications, 155(2), 937-942.

Hasabelnaby et al., (2012) Synthesis, chemical and enzymatic hydrolysis, and aqueous solubility of amino acid ester prodrugs of 3-carboranyl thymidine analogs for boron neutron capture therapy of brain tumors. European journal of medicinal chemistry, 55, 325-334.

Heinemann et al., (1988) Comparison of the cellular pharmacokinetics and toxicity of 2', 2'-difluorodeoxycytidine and 1-β-d-arabinofuranosylcytosine. Cancer research, 48(14), 4024-4031.

Hertel et al., (1990) Evaluation of the antitumor activity of gemcitabine (2', 2'-difluoro-2'-deoxycytidine). Cancer research, 50(14), 4417-4422.

Ho, (1974) Biochemical studies of a new antitumor agent, O2, 2'-cyclocytidine. Biochemical pharmacology, 23(8), 1235-1244.

Jin et al., (2008) Synthesis and In-vitro Evaluation of N4-Amino Acid Derivatives of Cytarabine for Improving the Oral Delivery of Cytarabine. Journal of Pharmaceutical Investigation, 38(4), 255-259.

Kodama et al., (1989) Antitumor Activity and Pharmacology of 1-β-D-Arabinofuranosylcytosine-5'-stearylphosphate: An Orally Active Derivative of 1-β-D-Arabinofuranosylcytosine. Cancer Science, 80(7), 679-685.

Liu et al., (2009) Synthesis and evaluation of anti-tumor activities of N4 fatty acyl amino acid derivatives of 1-β-arabinofuranosylcytosine. European journal of medicinal chemistry, 44(9), 3596-3600.

Manfredini et al., (2000) Peptide T-araC conjugates: solid-phase synthesis and biological activity of N4-(acylpeptidyl)-araC. Bioorganic & medicinal chemistry, 8(3), 539-547.

Patel (2014) Targeting GRP78 in Cancer with Nucleic Acid Bioconjugates. Ph.D. Thesis. Seton Hall University South orange, NJ, USA, 155 pages.

Piek et al., (1987) Cerebrospinal fluid and plasma aminograms in patients with primary and secondary tumors of the CNS. Infusionstherapie and klinische Emahrung, 14(2), 73-77. Abstract.

Singh et al., (2015) Development of reversible glutamine conjugate of methotrexate for enhanced brain delivery. Medicinal Chemistry Research, 24(2), 624-635.

Stammer et al., (1978) 5-Carboxamido-4-amino-3-isoxazolidone, an asparagine analog. Journal of medicinal chemistry, 21(7), 709-712.

Warrell Jr, et al., (1986) Phase I and II study of fludarabine phosphate in leukemia: therapeutic efficacy with delayed central nervous system toxicity. Journal of Clinical Oncology, 4(1), 74-79. Abstract.

Wechter et al., (1976) Nucleic acids. 16. Orally active derivatives of ara-cytidine. Journal of medicinal chemistry, 19(8), 1013-1017.

Woodcock et al., (1980) Biochemical, pharmacological, and phase I clinical evaluation of pseudoisocytidine. Cance research, 40(11), 4243-4249.

Renis, et al., "Antiviral Activity of Cytarabine in Herpesvirus-Infected Rats", Antimicrobial Agents and Chemotherapy, vol. 4, No. 4, Oct. 1, 1973 (Oct. 1, 1973), pp. 439-444.

Anonymous, "Study Evaluating the Safety and Efficacy of Astarabine in Acute Myeloid Leukemia or Acute Lymphoblastic Leukemnia (BSTPHASE1-01)", Clinical Trials.gov, Sep. 9, 2015 (Sep. 9, 2015), pp. 1-7, retrieved Jun. 3, 2019, https://clinicaltrials.gov/ct2/show/record/NCT02544438?view=record.

Tsila et al., "Astarabine, a Pro-Drug of Cytarabine, Is Safe for Patients with Advanced Acute Leukemia, a Phase I/IIa Single Center Study in Relapsed/Refractory or Medically Unfit Patients", Database Biosis, Biosciences Infor [ Online], Dec. 3, 2015.

Beran, M., Shen, Y., Kantarjian, H., O'Brien, S., Koller, C. A., Giles, F. J., . . . & Estey, E. H. (2001). High-dose chemotherapy in high-risk myelodysplastic syndrome: Covariate-adjusted comparison of five regimens. Cancer, 92(8), 1999-2015.

Cheon, E. P., Hong, J. H., & Han, H. K. (2006). Enhanced cellular uptake of Ara-C via a peptidomimetic prodrug, L-valyl-ara-C in Caco-2 cells. Journal of pharmacy and pharmacology, 58(7), 927-932.

Döhner, H., Lübbert, M., Fiedler, W., Fouillard, L., Haaland, A., Brandwein, J. M., . . . & Müller-Tidow, C. (2014). Randomized, phase 2 trial of low-dose cytarabine with or without volasertib in AML patients not suitable for induction therapy. Blood, 124(9), 1426-1433.

Extended European Search Report for corresponding European Patent Application No. EP16870114.2 dated Jun. 17, 2019.

Extended European Search Report for corresponding European Patent Application No. EP16870129.0 dated Jun. 21, 2019.

Fasinu, P., Pillay, V., Ndesendo, V. M., du Toit, L. C., & Choonara, Y. E. (2011). Diverse approaches for the enhancement of oral drug bioavailability. Biopharmaceutics & drug disposition, 32(4), 185-209.

Gengrinovitch, S., Yakar, R. B., Zuckerman, T., Krivoy, N., & Rowe, J. M. (Dec. 3, 2015), "Astarabine, a Cytarabine Pro-Drug, Is Safe and Efficacious in the Treatment of Leukemia-Results of Animal Studies". Blood, vol. 126, No. 23, pp. 2545. 57th Annual Meeting of the American Society of Hematology, ASH 2015, San Diego, CA, United States.

International Search Report for PCT Application No. PCT/IL2016/050077 dated May 16, 2016.

International Search Report for PCT Application No. PCT/IL2016/051287 dated Mar. 26, 2017.

Kato, Y., Saito, M., Fukushima, H., Takeda, Y., & Hara, T. (1984). Antitumor activity of 1-β-d-arabinofuranosylcytosine conjugated with polyglutamic acid and its derivative. Cancer research, 44(1), 25-30.

Löwenberg, B., Pabst, T., Vellenga, E., van Putten, W., Schouten, H. C., Graux, C., . . . & de Greef, G. E. (2011). Cytarabine dose for acute myeloid leukemia. New England Journal of Medicine, 364(11), 1027-1036.

Novotny, L., & Rauko, P. (2009). Cytarabine conjugates with biologically active molecules and their potential anticancer activity. Neoplasma, 56(3), 177-186.

Zuckerman T. (Sep. 9, 2015). Study Evaluating the Safety and Efficacy of Astarabine in Acute Myeloid Leukemia or Acute Lymphoblastic Leukemia (BSTPHASE1-01), BioSight Ltd., ClinicalTrials.gov Identifier: NCT02544438, retrieved on-line at: https://clinicaltrials.gov/ct2/show/NCT02544438.

Burk, M., Heyll, A., Arning, M., Volmer, M., Fartash, K., & Schneider, W. (1997). Pharmacokinetics of high-dose cytarabine and its deamination product—a reappraisal. Leukemia & lymphoma, 27(3-4), 321-327.

Capizzi, R. L., Yang, J. L., Cheng, E., Bjornsson, T., Sahasrabudhe, D., Tan, R. S., & Cheng, Y. C. (1983). Alteration of the pharmacokinetics of high-dose ara-C by its metabolite, high ara-U in patients with acute leukemia. Journal of Clinical Oncology, 1(12), 763-771.

DeAngelis, L. M., Kreis, W., Chan, K., Dantis, E., & Akerman, S. (1992). Pharmacokinetics of ara-C and ara-U in plasma and CSF after high-dose administration of cytosine arabinoside. Cancer chemotherapy and pharmacology, 29(3), 173-177.

Reese, N. D., & Schiller, G. J. (2013). High-dose cytarabine (HD araC) in the treatment of leukemias: a review. Current hematologic malignancy reports, 8(2), 141-148.

Zuckerman, T., Ram, R., Akria, L., Koren-Michowitz, M., Hoffman, R., Henig, I., . . . & Tavor, S. (2019). BST-236, a novel cytarabine

(56) References Cited

OTHER PUBLICATIONS prodrug for patients with acute leukemia unfit for standard induction: a phase 1/2a study. Blood advances, 3(22), 3740-3749.
Bishop, J. F. et al. (1996). A randomized study of high-dose cytarabine in induction in acute myeloid leukemia. *Blood*, 87(5), 1710-1717.
Day, C. P. et al. (2015). Preclinical mouse cancer models: a maze of opportunities and challenges. *Cell*, 163(1), 39-53.
Ferreri, A. J. et al. (2009). High-dose cytarabine plus high-dose methotrexate versus high-dose methotrexate alone in patients with primary CNS lymphoma: a randomised phase 2 trial. *The Lancet*, 374(9700), 1512-1520.
Singh, M. et al. (2012). Modeling and predicting clinical efficacy for drugs targeting the tumor milieu. *Nature Biotechnology*, 30(7), 648-657.
Wall, R. J. et al. (2008). Are animal models as good as we think?. *Theriogenology*, 69(1), 2-9.

* cited by examiner

SALTS OF CONJUGATES FOR CANCER THERAPY

CROSS REFERENCE TO RELATED APPLICATIONS

This application is a National Phase Application of PCT International Application No. PCT/IL2016/051287, International Filing Date Dec. 1, 2016, claiming benefit of U.S. Patent Application No. 62/370,257, filed Aug. 3, 2016, and of U.S. Patent Application No. 62/262,428, filed Dec. 3, 2015, which are hereby incorporated by reference.

FIELD OF THE INVENTION

The present invention relates to pharmaceutically acceptable salts of conjugates comprising a chemotherapeutic drug and an amino acid or a derivative thereof, which are readily taken up by a cancer cell. In particular, the present invention relates to pharmaceutically acceptable salts of conjugates of cytidine analog drugs and aspartic or glutamic acid and analogs thereof, pharmaceutical compositions comprising these conjugates and use thereof for the treatment of cancer or a pre-cancer condition or disorder.

BACKGROUND OF THE INVENTION

Anti-Proliferative Drugs

Anti-proliferative drugs, also known as anti-metabolites, anti-neoplastic agents and covalent DNA binding drugs, act by inhibiting essential metabolic pathways and are commonly used in the treatment of malignant diseases. However, their high toxicity to normal cells and severe side effects limit their use as therapeutic agents. Undesirable side effects include anemia, emesis and balding due to cytotoxic effects on rapidly dividing normal cells, such as stem cells in the bone marrow, epithelial cells of the intestinal tract, hair follicle cells, etc.

Another major problem associated with anti-proliferative drugs is inherent or acquired resistance of tumors to the drugs. For example, although the initial remission rate following treatment with L-asparaginase is quite high in acute lymphoblastic leukemia (ALL) patients, relapse and associated drug resistance pose a significant clinical problem. Studies have demonstrated increased asparagine synthetase (AS) expression in asparaginase-resistant cells, which has led to the hypothesis that elevated AS activity permits drug-resistant survival of malignant cells.

Nucleotide/Nucleoside Analogs

Nucleoside analogs compete with their physiologic counterparts for incorporation into nucleic acids and have earned an important place in the treatment of acute leukemia. The most important of these are the arabinose nucleosides; a unique class of antimetabolites originally isolated from the sponge Cryptothethya crypta, but now produced synthetically. They differ from the physiologic deoxyribonucleosides by the presence of a 2'-OH group in the cis configuration relative to the N-glycosyl bond between cytosine and arabinoside sugar. Several arabinose nucleosides have useful antitumor and antiviral effects. The most active cytotoxic agent of this class is cytosine arabinoside (cytarabine). A related nucleoside, adenine arabinoside, also exerts antitumor activity, and its analog, Fludarabine phosphate (2-fluoro-ara-adenosine mono-phosphate), has strong antitumor activity in lymphomas and in chronic lymphocytic leukemia (Warrell & Berman, 1986). Another member of the group is arabinosyl-5-azacytidine, a synthetic analog that failed in the clinic (Dalal et al, 1986).

One objective of analog development in the area of cytidine antimetabolites has been to find compounds that preserve the inhibitory activity of ara-C but are resistant to deamination. A number of deaminase-resistant analogs have been developed, including cyclo-cytidine (Ho DHW, 1974) and $N^4$-behenoyl ara-C (Kodama et al., 1989) that showed anti-leukemic activity in some clinical trials, but had undesirable side effects (Woodcock et al., 1980). Other representative compounds are $N^4$-Palmitoyl-ara, 2'-Azido-2'-deoxy ara-C, 5'-(Cortisone 21-phosphoryl) ester of ara-C, 5'-Acyl esters of ara-C (e.g., 5'-palmitate ester), $N^4$ Behenoyl-ara-C, Ara-C conjugate with poly-$H^5$ (2-hydroxyethyl)-L-glutamine, Dihydro-5-azacytidine, 5-Aza-arabinosylcytosine, 5-Aza 2'-deoxycytidine and 2'-2'-Difluorodeoxycytidine (Hartel et al., 1990 and Heineman et al., 1988).

Gemcitabine (2,2-difluorodeoxycytidine, dFdC) is the most important cytidine analog to enter clinical trials since ara-C. It has become incorporated into the standard first-line therapy for patients with pancreatic cancer, lung cancer, and transitional cell cancer of the bladder.

Nucleotide analogs have also been used in non-cancer applications. For example Flucytosine, a fluorinated cytosine analog, is used as an antifungal agent.

Amino Acids and Proliferative Disease

Asparagine is a non-essential amino acid that is required by rapidly proliferating cells. Mammalian cells can synthesize asparagine from aspartate using the ATP-dependent enzyme asparagine synthetase (CE 6.3.5.4), which transfers the amino group from the amide of glutamine to the β-carboxyl of aspartate in a reaction that may be represented as:
Glutamine+Aspartate+ATP+$H_2$O=Glutamate+Asparagine+AMP+PPi.

Asparagine synthetase deficiency occurs in certain tumors, causing them to rely on an external supply of asparagine from other sources, such as serum. This observation led to the development of the enzyme L-asparaginase (type CE-2, CE 3.5.1.1) as a chemotherapeutic agent. L-asparaginase hydrolyzes L-asparagine to aspartate and ammonia, hence depleting L-asparagine from the serum and inhibiting tumor growth. L-asparaginase is used mainly in the treatment of Acute Lymphoblastic Leukemia (ALL) and shows some activity against other hematological cancers including acute non-lymphocytic leukemia.

The L-asparaginase used in the clinic is available in two unmodified (native) forms purified from bacterial sources, and one as a PEGylated compound. U.S. Pat. No. 4,179,337 teaches PEGylated L-asparaginase, wherein the enzyme is coupled to PEG having a molecular weight of about 500 to 20,000 Daltons.

The in vivo down-regulation of asparagine synthetase may provide an efficient mechanism for inhibiting tumor growth. However, cells respond to amino acid deprivation by a concerted increase in asparagine synthetase mRNA, protein, and enzymatic activity that involves transcriptional control of the asparagine synthetase gene.

A metabolic approach was initially used to inhibit the activity of asparagine synthetase by the generation of L-asparagine and L-aspartic acid analogs. Analogs including 5-carboxamido-4-amino-3-isoxazolidone (Stammer et al., 1978) and N-substituted sulfonamides and N'-substituted sulfonylhydrazides have been prepared as sulfur analogues of L-asparagine (Brynes S et al., 1978a; Brynes S et al., 1978b). U.S. Pat. No. 4,348,522 teaches the salt of PALA, N-phosphonacetyl-L-aspartic acid, which has been shown to exhibit anti-tumor activity and is presently in clinical trials as combination chemotherapy for colorectal and pancreatic cancers.

Aspartic acid analog of Ara-C was used as a raw material for further synthesis of peptide T Ara-C conjugates for targeting CD4 positive cells (Manfredini et at, 2000).

The use of prodrugs to impart desired characteristics such as increased bioavailability or increased site-specificity is a recognized concept in the art of pharmaceutical development. For example, direct or indirect conjugation of a drug to an antibody creates a stable conjugate that can arrive at the target site with minimum dissociation of the drug. Drug targeting may be combined with a mechanism of selective release of the drug for maximal potency.

U.S. Pat. No. 4,296,105 describes doxorubicin derivatives linked to an optionally substituted amino acid at the hydroxy group of the amino acid residue, which possess in vitro a higher antitumor activity and lower toxicity than doxorubicin.

U.S. Pat. No. 5,962,216 teaches tumor activated prodrugs which are unable to enter the cell until cleaved by a factor or factors secreted by a target cell.

U.S. Pat. No. 5,650,386 teaches compositions comprising at least one active agent, and at least one modified non-alpha amino acid or poly amino acid, which acts as a carrier of the active agent. The amino acid modification includes acylation or sulfonation of at least one free amine group.

U.S. Pat. Nos. 6,623,731, 6,428,780 and 6,344,213 teach non-covalent mixtures comprising modified amino acids as carriers for biologically active agents.

U.S. Pat. No. 5,106,951 discloses a conjugate comprising an aromatic drug non-covalently intercalated between two aromatic side chains on an oligopeptide, and an antibody or antibody fragment covalently attached to the oligopeptide for targeting to cancer cells.

U.S. Pat. No. 6,617,306 teaches a carrier for the in vivo delivery of a therapeutic agent, the carrier and therapeutic agent linked by a disulfide bond. In that patent, the carrier comprises a polymer, and at least one thiol compound conjugated to the polymer, such that the thiol group of the thiol compound and the thiol group of the therapeutic agent form a disulfide bond.

International patent application publication No. WO 00/33888 teaches cleavable anti-tumor and anti-inflammatory compounds comprising a therapeutic agent capable of entering a target cell, an oligopeptide, a stabilizing group and an optional linker.

International patent application publication No. WO 2005/072061 and U.S. Pat. No. 7,989,188 to some of the inventors of the present invention describe compounds comprising a drug covalently linked to an amino acid via a side chain with a functional group useful for targeting drugs to neoplastic cells.

Pharmaceutical Salts

Selection of optimal pharmaceutical salts of a drug may increase the efficacy and improve drug delivery of the drug. The establishment of such active drug salts is not trivial and requires unique methods in the development and analysis of such salts.

There remains an unmet medical need for compounds and compositions capable of targeting tumors while obviating cytotoxic damage to normal tissues.

SUMMARY OF THE INVENTION

It is an object of the present invention to target drugs to malignant and pre-malignant cells while reducing the side effects associated with the current drug therapy.

The present invention provides pharmaceutically acceptable salts of conjugates comprising a first chemical moiety covalently linked to a second chemical moiety, wherein the first chemical moiety is an amino acid comprising on its side chain at least one functional group selected from the group consisting of an amino group, a carboxyl group, a sulfhydryl group and a hydroxyl group, and the second chemical moiety is an anti-cancer drug selected from the group consisting of a cytotoxic agent, a cytostatic agent and a chemotherapeutic agent. The anti-cancer drug is attached to the amino acid through the amino acid side chain functional group. The amino acid is preferably aspartic acid or glutamic acid or derivatives or analogs thereof covalently linked to the anti-cancer drug, preferably a nucleotide/nucleoside analog such as cytarabine or gemcitabine. The pharmaceutically acceptable salt is preferably selected from organic or inorganic acid or residue of an acid (i.e., its conjugate base). The present invention further provides pharmaceutical compositions comprising the conjugate salts, and use thereof for treating cancer and pre-cancer conditions or disorders. The present invention further provides methods for preparing the salt forms of the conjugates of the present invention, in particular reacting a protected precursor compound with an acid that forms the relevant salt.

The salt forms of the present invention may serve as a delivery vehicle for a drug or prodrug in which the drug undergoes rapid uptake by cancer cells. The salt forms may also serve to increase the stability and solubility of the conjugate.

The conjugates of the present invention are typically prepared from precursors which contain one or more protecting groups on susceptible moieties such as amines or carboxylic acids. For example, the amino group of the amino acid is typically protected by a t-butoxycarbonyl (BOC) group. It is well known that BOC groups are typically removed from amino groups in acid media, with trifluoroacetic acid (TFA) being the most commonly used deprotecting agent. It is further known that TFA is difficult to remove, and therefore the deprotected amines usually contain residual amounts of TFA. Due to its toxic effects, compounds which are devoid of TFA are required for pharmaceutical use. In some embodiments, the present invention avoids the need of using TFA as a deprotecting agent. It has now been unexpectedly discovered that salts of the conjugates of the present invention can be prepared by deprotecting BOC groups using the same reagent that ultimately forms the salt. It is now disclosed that certain pharmaceutically acceptable acids can simultaneously remove the protecting group(s) and generate the salt of the conjugate of the present invention in one step, thereby obviating an intermediate step of deprotection by TFA prior to salt formation. Thus, in certain embodiments, the conjugates of the present invention are not exposed to TFA for deprotection, and thus the conjugate salts of the present invention are free of TFA remnants. The resulting salts are therefore highly advantageous by virtue of being devoid of the toxic TFA and hence are suitable for pharmaceutical use.

According to a first aspect, the present invention provides a pharmaceutically acceptable salt of a compound, the salt represented by the structure of formula (I)

$$A\text{-}D.Y \tag{I}$$

wherein,

A denotes an amino acid comprising on its side chain at least one functional group selected from the group consisting of a carboxyl group, an amino group, a sulfhydryl group and a hydroxyl group;

D denotes a residue of a drug selected from the group consisting of a cytotoxic agent, a cytostatic agent and a chemotherapeutic agent, wherein D is attached to A through the side chain functional group of A; and Y is a pharmaceutically acceptable organic or inorganic acid or residue of an acid (i.e., the conjugate base of said acid), selected from the group consisting of hydrochloric acid, acetic acid, methanesulfonic acid, phosphoric acid, citric acid, lactic acid, succinic acid, tartaric acid, boric acid, benzoic acid, toluenesulfonic acid, benzenesulfonic acid, ascorbic acid, sulfuric acid, maleic acid, formic acid, malonic acid, nicotinic acid and oxalic acid, wherein the pharmaceutically acceptable salt contains 0.1% or less trifluoroacetic acid (TFA) as an impurity. Each possibility represents a separate embodiment of the present invention.

The amino acid (A) may be an α-amino acid (D or L), β-amino acid, γ-amino acid, δ-amino acid or ε-amino acid. In one currently preferred embodiment, the amino acid (A) is an α-amino acid (D or L). In some embodiments, the amino acid (A) is selected from the group consisting of aspartic acid (Asp), glutamic acid (Glu), asparagine (Asn), glutamine (Gln), α-aminoadipic acid (Aad), α-aminopimelic, γ-carboxy-glutamic acid, γ-hydroxy-glutamic acid, aminoglycine, aminoisobutyric acid (Aib), arginine (Arg), citrulline (Cit), cysteine (Cys), cystine, diaminobutanoic acid, diaminobutyric acid (Dab), diaminopropionic acid (Dpr), dihydroxyphenylalanine, dimethylarginine, pyroglutamic acid (p-Glu), histidine (His), 1-methyl-histidine, 3-methyl-histidine, homoserine (Hse), homocitrulline, hydroxyproline (Hyp), lysine (Lys), methyl-lysine, dimethyl lysine, trimethyl lysine, azidolysine, methionine (Met), methionine-sulfoxide, methionine-sulfone, ornithine (Orn), sarcosine (Sar), Selenocystein (Sec), serine (Ser), phosphorserine, methyl-serine, aminoserine (Ams), thienylalanine (Thi), threonine (Thr), phospho-threonine, tryptophan (Trp), tyrosine (Tyr), methyl-tyrosine, phosphor-tyrosine, sulfotyrosine, α-aminosuberic acid, 3,5-diiodotyrosine, penicillamine (Pen), 4-ethylamine phenylglycine, 4-aminophenylglycine, 4-sulfophenylalanine, 4-aminophenylalanine and 2-amino-4[4-(2-amino)-pyrimidinyl]butanoic acid, 3-aminopropionic acid, 6-aminohexanoic acid (ε-Ahx), p-aminobenzoic acid, isonipecotic acid, statine (Sta), 2-aminobutyric acid (Abu) and 4-aminobutyric acid, and derivatives and analogs thereof. Each possibility represents a separate embodiment of the present invention.

In some embodiments, the amino acid (A) is selected from the group consisting of aspartic acid, glutamic acid, asparagine, glutamine, and derivatives and analogs thereof. In one currently preferred embodiment, the amino acid (A) is aspartic acid. In another currently preferred embodiment, the amino acid (A) is glutamic acid.

The group (D) may be derived from any drug selected from the group consisting of a cytotoxic agent, a cytostatic agent and a chemotherapeutic agent. In some embodiments, the cytotoxic, cytostatic or chemotherapeutic agent D is the residue of a drug selected from the group consisting of a pyrimidine analog, a purine analog, an antifolate, hydroxyurea, an antimicrotubule agent, an alkylating agent, an antitumor antibiotic, a topoisomerase targeting agent, an antimetabolite, a DNA binding agent and a DNA antagonist.

In some embodiments, the cytotoxic, cytostatic or chemotherapeutic agent D is the residue of a pyrimidine analog selected from cytosine arabinoside (ara-C, cytarabine), gemcitabine, fluorouracil, 5-fluorodeoxyuridine (5-FUDR), ftorafur, capecitabine, carmofur, BOF-A2, 5-chloro-2,4-dihydroxypyridine, decitabine, leflunomide, trifluridine, iodoxuridine, zidovudine, telbivudine, trimethoprim, fluorocytosine, deoxythymidine and 5-amino-6-nitro uracil. Each possibility represents a separate embodiment of the present invention. In one currently preferred embodiment, the cytotoxic, cytostatic or chemotherapeutic agent D is the residue of cytarabine. In another currently preferred embodiment, the cytotoxic, cytostatic or chemotherapeutic agent D is the residue of gemcitabine.

In other embodiments, the cytotoxic, cytostatic or chemotherapeutic agent D is the residue of a purine analog selected from clofarabine, decarbazine, cladribine, mercaptopurine, nelarabine, pentostatine, thioguanine, gefitinib, azathiopurine, 8-azaguanine, immucillin-G, 2-fluoro-2'-deoxyadenosine, 9-beta-D-xylofuranosyl-adenine, 3-dexoxyguanine, 6-methyl-formycin A, 2-fluoroadenosine, 1-deaza-adenosine, N-ethyl-5-carboxamido-adenosine, 3'-oxo-adenosine, 2-amino-adenosine, 6-O-cyclomethylguanine fludarabine, and 8-iodo-guanine. Each possibility represents a separate embodiment of the present invention.

In other embodiments, the cytotoxic, cytostatic or chemotherapeutic agent D is the residue of a drug selected from the group consisting of 2,4-dioxo-5-fluoropyrimidine (5-FU), azacytidine (5-AZC), 6-mercaptopurine (6-MP), 6-thioguanine (6-TG), chlorodeoxyadenosine (2-CDA) and pentostatin (dCF). Each possibility represents a separate embodiment of the present invention.

In some embodiments, the salts of formula (I) are prepared in a substantially pure form. The term "substantially pure" refers to at least 95% purity as determined by HPLC, preferably at least about 97% purity, more preferably at least 98% purity, and most preferably at least 99% purity.

As noted above, in the conjugates of the present invention, the cytotoxic, cytostatic or chemotherapeutic agent D is attached to the amino acid (A) through the side chain functional group of (A). Some non-limiting embodiments of such conjugates are described below. According to some embodiments, the amino acid (A) is selected from the group consisting of aspartic acid and glutamic acid, and the compound is represented by the structure of formula (II) or (III):

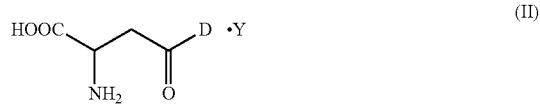
(II)

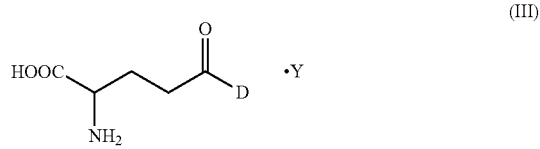
(III)

wherein D and Y are as defined above.

In a specific embodiment of formula (II), A is aspartic acid and D is the residue of cytarabine. In this embodiment, the compound is a salt represented by the structure of formula (1):

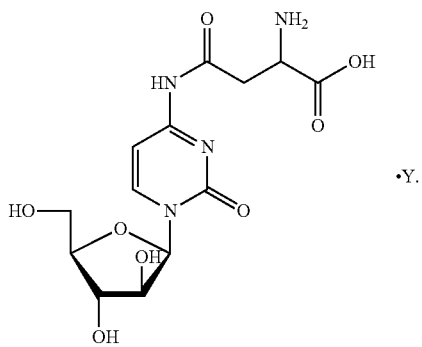

(1)

In one embodiment of formula (1), the compound is a salt with acetic acid (i.e., an acetate salt), which is represented by the structure of formula (1A):

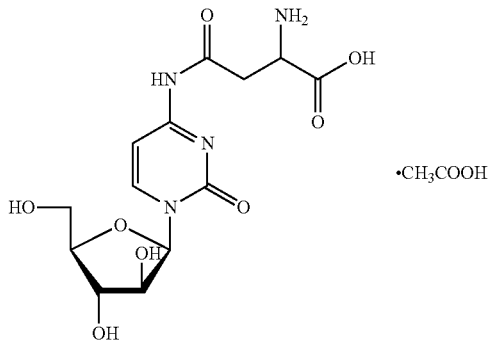

(1A)

In another embodiment of formula (1), the compound is a salt with hydrochloric acid (i.e., a hydrochloride salt), which is represented by the structure of formula (1B):

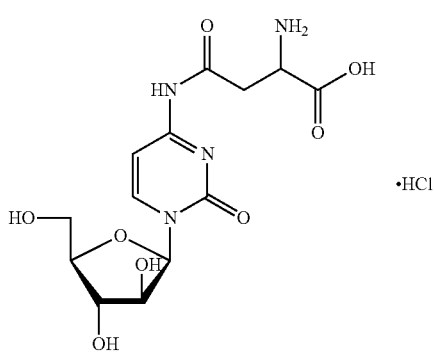

(1B)

In another specific embodiment of formula (II), A is aspartic acid and D is the residue of gemcitabine, and the compound is represented by the structure of formula (2):

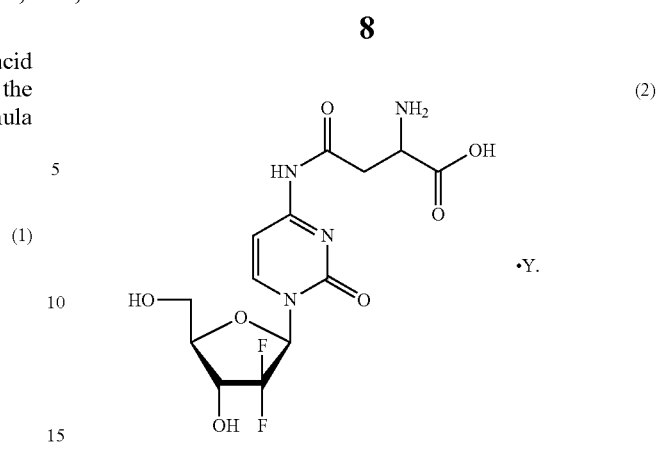

(2)

In a specific embodiment of formula (III), A is glutamic acid and D is the residue of cytarabine, and the compound is represented by the structure of formula (3):

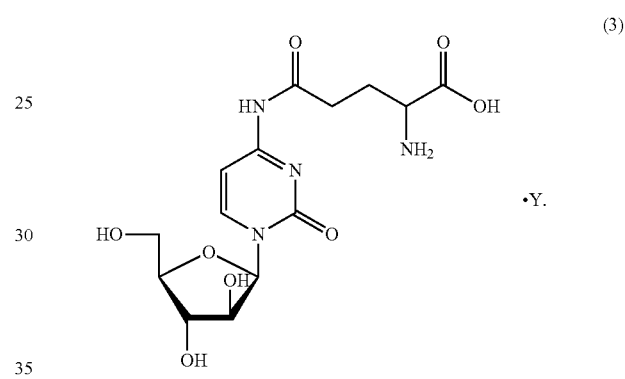

(3)

In another specific embodiment of formula (III), A is glutamic acid and D is the residue of gemcitabine, and the compound is represented by the structure of formula (4):

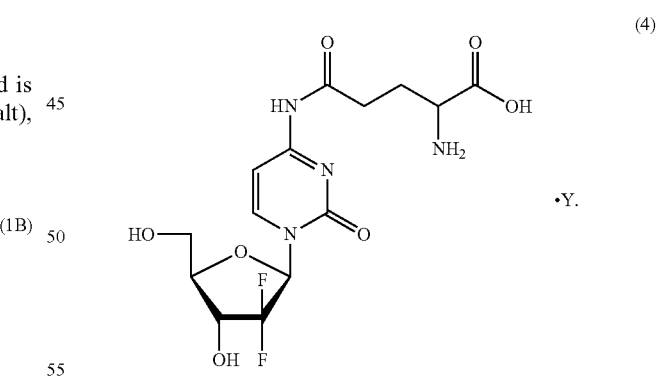

(4)

In any of the aforementioned compounds of formula (I), (II), (III), (1), (2), (3) and (4), Y is a pharmaceutically acceptable acid selected from the group consisting of acetic acid, hydrochloric acid, methanesulfonic acid, phosphoric acid, citric acid, lactic acid, succinic acid, tartaric acid, boric acid, benzoic acid, toluenesulfonic acid, benzenesulfonic acid, ascorbic acid, sulfuric acid, maleic acid, formic acid, malonic acid, nicotinic acid and oxalic acid. Each possibility represents a separate embodiment of the present invention.

In one currently preferred embodiment, the pharmaceutically acceptable acid Y is acetic acid, i.e., an organic acid.

In another currently preferred embodiment, the pharmaceutically acceptable acid Y is hydrochloric acid (HCl), i.e., an inorganic acid.

It is understood by a person of skill in the art that any one of the above mentioned pharmaceutically acceptable acids can form a pharmaceutically acceptable salt with the compounds of the invention. In some embodiments, the pharmaceutically acceptable salt is selected from the group consisting of: acetate, hydrochloride, methanesulfonate, phosphate, citrate, lactate, succinate, tartarate, borate, benzoate, toluenesulfonate, benzensulfonate, ascorbate, sulfate, maleate, formate, malonate, nicotinate and oxalate. Each possibility represents a separate embodiment of the present invention.

In one currently preferred embodiment, the pharmaceutically acceptable acid is acetic acid ($CH_3COOH$). In this embodiment, the salt is an acetate salt. In another preferred embodiment, the pharmaceutically acceptable salt is a hydrochloric acid (HCl) salt. In this embodiment, the salt is a hydrochloride salt.

In another aspect, the present invention provides a pharmaceutical composition comprising as an active ingredient a salt of formula (I), or any compound covered by such formula, e.g., compounds (II), (III), (1), (1A), (1B), (2), (3) or (4), as described herein and a pharmaceutically acceptable carrier or diluent.

In another aspect, the present invention provides a method of treating a cancer including metastases thereof, comprising the step of administering to a subject in need thereof a therapeutically effective amount of a salt of formula (I), or any compound covered by such formula, e.g., compounds (II), (III), (1), (1A), (1B), (2), (3) or (4), as described herein. In another aspect, the present invention provides a salt of formula (I), or any compound covered by such formula, e.g., compounds (II), (III), (1), (1A), (1B), (2), (3) or (4), as described herein, for use in treating a cancer including metastases thereof. In some embodiments, the cancer is characterized by a non-solid tumor or a solid tumor or a combination thereof.

In other embodiments, the cancer is a hematological cancer. In other specific embodiments, the hematological cancer is selected from the group consisting of leukemias, lymphomas and multiple myeloma. In some embodiments, the leukemia is selected from the group consisting of acute myeloid leukemia (AML) and acute lymphoblastic leukemia (ALL). In some embodiments, the leukemia is a relapsed/refractory leukemia. In other embodiments, the leukemia is newly diagnosed leukemia.

In some specific embodiments, the cancer characterized by a solid tumor is selected from the group consisting of tumors in the central nervous system (CNS), liver cancer, colorectal carcinoma, breast cancer, gastric cancer, pancreatic cancer, bladder carcinoma, cervical carcinoma, head and neck tumors, vulvar cancer and dermatological neoplasms including melanoma, squamous cell carcinoma and basal cell carcinomas.

In another aspect, the present invention provides a method of treating a pre-cancer condition or disorder, comprising the step of administering to a subject in need thereof a therapeutically effective amount of a salt of formula (I), or any compound covered by such formula, e.g., compounds (II), (III), (1), (1A), (1B), (2), (3) or (4), as described herein.

In another aspect, the present invention provides a salt of formula (I), or any compound covered by such formula, e.g., compounds (II), (III), (1), (1A), (1B), (2), (3) or (4), as described herein, for use in treating a pre-cancer condition or disorder.

In some embodiments, the pre-cancer condition or disorder is Myelodysplastic Syndromes (MDS).

In other embodiments, the present invention relates to a method of treating an individual who is a candidate for a bone marrow transplant, comprising the step of pre-treating said individual, prior to the transplant, with a salt of formula (I), or any compound covered by such formula, e.g., compounds (II), (III), (1), (1A), (1B), (2), (3) or (4), as described herein.

In other embodiments, the present invention provides a salt of formula (I), or any compound covered by such formula, e.g., compounds (II), (III), (1), (1A), (1B), (2), (3) or (4), as described herein, for use in pre-treatment prior to a bone marrow transplant.

The salt forms of the present invention may be used to treat any mammal, preferably humans.

Further disclosed is a method for preparing a pharmaceutically acceptable salt of a compound represented by formula (I) of the present invention, comprising the step of (a) reacting a compound of the formula (IV):

$$(A\text{-}D)\text{-}(P)_n \qquad (IV)$$

wherein
A and D are as defined above;
n is an integer of 1-6; and
each P is independently at each occurrence a protecting group; wherein each P is attached to any functional group available for protection on the amino acid (A), the drug residue (D) or to both the amino acid (A) and the drug residue (D);
with a reagent capable of removing the protecting group(s) P; and
(b) adding a reagent capable of introducing the group Y, so as to generate a salt represented by the formula:

$$A\text{-}D.Y \qquad (I)$$

wherein Y is as defined above.

In one embodiment, it has now been unexpectedly discovered that the salts of the present invention can be prepared by deprotecting a precursor compound using the same pharmaceutically acceptable acid that ultimately forms the salt. Thus, according to the principles of the present invention, the pharmaceutically acceptable acid Y capable of introducing the group Y can simultaneously remove the protecting group(s) P and generate the salt of formula (I) in one step, thereby obviating an intermediate step of deprotection prior to salt formation. In this way, the purity level of the salt product is improved as residual amounts of deprotecting agent (i.e., impurities) are avoided. For example, protecting groups such as t-butoxycarbonyl (BOC) are typically removed in acid media, e.g., with trifluoroacetic acid (TFA). However, TFA is difficult to remove, and therefore the deprotected product includes residual amounts of this acid. This inevitably leads to increased TFA impurity levels in the final salt forms, which is unacceptable from a pharmaceutical development perspective. The present invention provides a solution to this problem by carrying out the final step of the synthesis using the same reagent (e.g., acid) that will ultimately form the salt.

Thus, in one embodiment, the process of the invention involves the use of a reagent capable of removing the protecting group(s) P and simultaneously introducing the group Y, e.g., an acid. In accordance with this embodiment, the protecting group(s) P are removed, and the group Y are introduced in one step.

According to some embodiments, the pharmaceutically acceptable salt of the conjugate of the present invention contains about 5% or less residual TFA. According to additional embodiments, the pharmaceutically acceptable salt of the conjugate of the present invention contains about 1% or less residual TFA. According to additional embodiments, the pharmaceutically acceptable salt of the conjugate of the present invention contains about 0.1% or less residual TFA. According to a certain embodiment, the pharmaceutically acceptable salt of the conjugate of the present invention is substantially devoid of TFA as an impurity. According to another embodiment, the pharmaceutically acceptable salt of the conjugate of the present invention is completely devoid of TFA as an impurity.

The compounds of formula (I) can generally be prepared by coupling a drug moiety with an amino acid, preferably in the presence of a coupling agent, and conversion to the salt form according to the process described above. This process is exemplified herein for compounds of formula (II) and (III).

In some embodiments, the present invention provides a process for preparing a compound of formula (II), comprising the step of:
(a) coupling a compound of formula (i) with a drug of formula D or a protected derivative thereof of formula D-$(P^3)_n$ in the presence of a coupling reagent to afford an intermediate of formula (ii); and
(b) removing the protecting groups $P^1$, $P^2$ and $P^3$ (if present), with an acid (Y) or with a deprotecting agent followed by an acid (Y) so as to generate a salt represented by the formula (II):

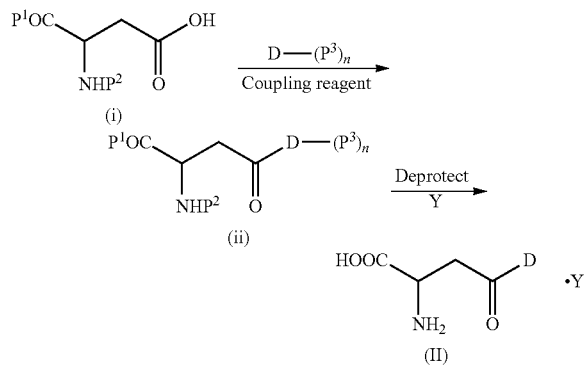

wherein $P^1$ is a carboxy protecting group, $P^2$ is an amino protecting group, $P^3$ is a protecting group located on one or more functional groups on the drug D, and n is 0, 1, 2 or 3.

In other embodiments, the present invention provides a process for preparing a compound of formula (III), comprising the step of:
(a) coupling a compound of formula (iii) with a drug of formula D or a protected derivative thereof of formula D-$(P^3)_n$ in the presence of a coupling reagent to afford an intermediate of formula (iv); and
(b) removing the protecting groups $P^1$, $P^2$ and $P^3$ (if present), with an acid (Y) or with a deprotecting agent followed by an acid (Y) so as to generate a salt represented by the formula (II)

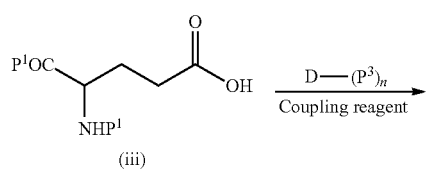

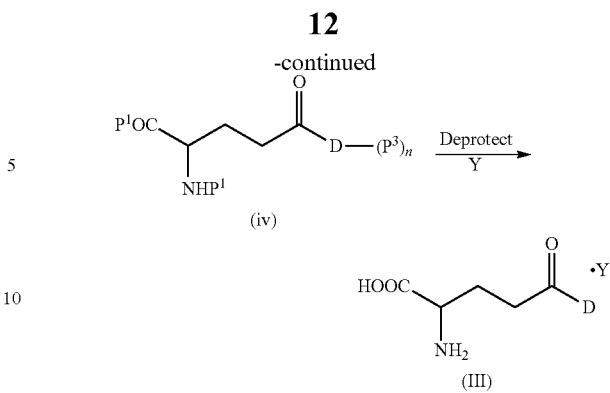

wherein $P^1$ is a carboxy protecting group, $P^2$ is an amino protecting group, $P^3$ is a protecting group located on one or more functional groups on the drug D, and n is 0, 1, 2 or 3.

In one embodiment, the drug is cytarabine. In other embodiments the drug is protected-cytarabine, comprising protecting groups on its 2', 3' and/or 5' hydroxyl moieties, such as triphenylmethyl-cytarabine (CAS 7075-13-0), benzoyl-cytarabine (CAS 34270-10-5), admantoyl-cytarabine (CAS 23113-01-1), and trimethylsilyl-cytarabine. In other embodiments, the drug is gemcitabine. In other embodiments the drug is a protected-gemcitabine comprising protecting groups on its 3' and/or 5' hydroxyl moieties, such as triphenylmethyl-gemcitabine (CAS 1642862-24-5).

In some embodiments, the protecting groups are removed simultaneously with introduction of the group Y, using an acid that is capable of removing the protecting groups and introducing the group Y.

These and other embodiments of the present invention will become apparent in conjunction with the figures, description and claims that follow.

DETAILED DESCRIPTION OF THE INVENTION

Figure 1:
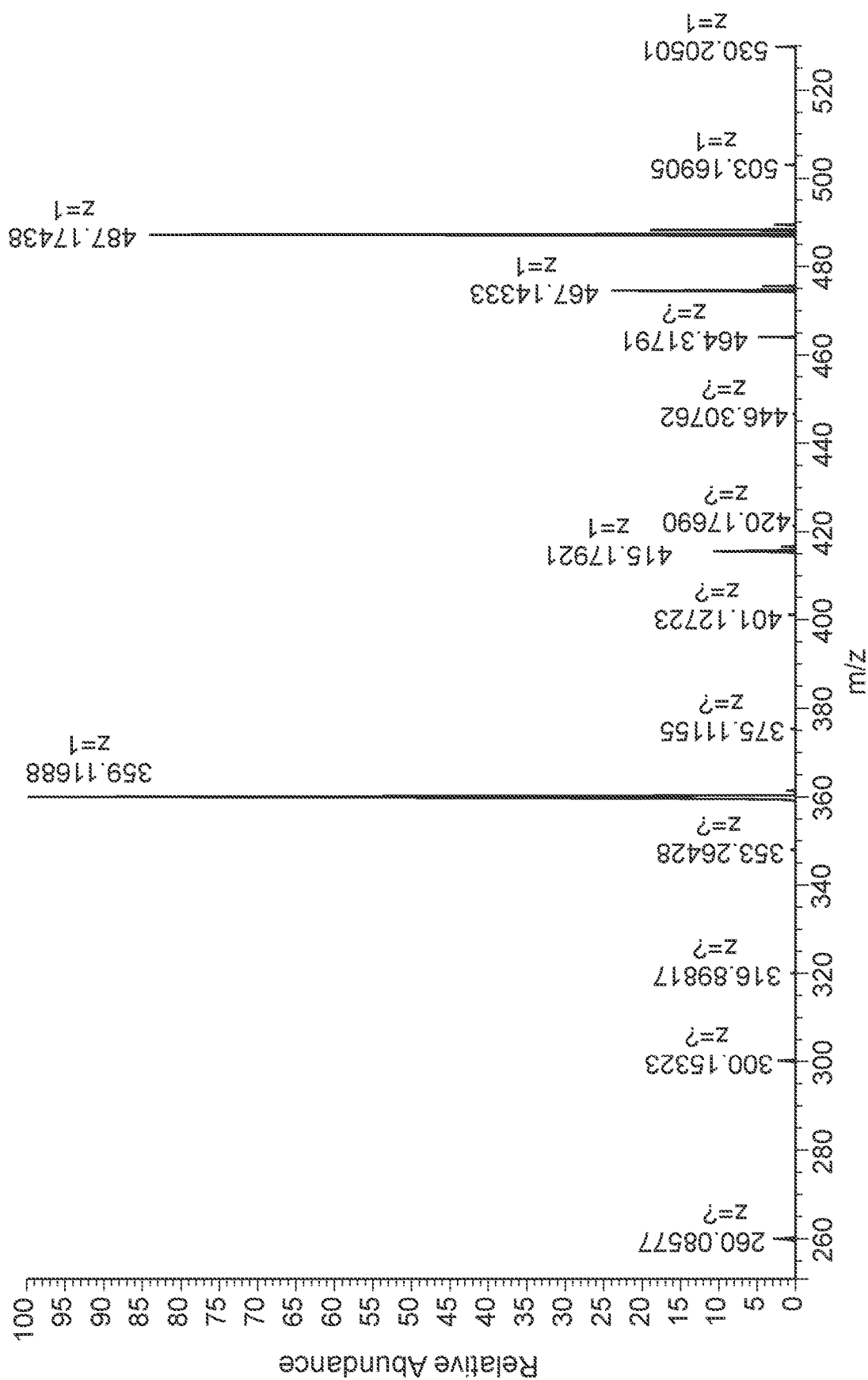
FIG. 1: Mass spectrum of Asp(Cytarabine).acetate salt (Y=$CH_3COOH$).

The present invention provides pharmaceutically acceptable salt forms of conjugates of amino acid covalently linked to therapeutic agents. In particular, the present invention relates to pharmaceutically acceptable salts of conjugates comprising cytidine analog drugs and aspartic or glutamic acid and analogs thereof, pharmaceutical compositions comprising these conjugates and use thereof for the treatment of cancer or a pre-cancer condition or disorder.

The art neither teaches nor suggests methods for creating acid addition salt forms of a drug covalently linked to an amino acid via a side chain functional group using direct transformation methods. The present invention discloses that pharmaceutical salts can be created from a precursor of the drug conjugate having protected groups removable by the same compound (e.g., acid) that is used to generate the pharmaceutical salt form.

Conjugates

The conjugates of the present invention are provided as pharmaceutically acceptable salt forms of conjugates, which are biologically active as inhibitors of proliferation of cancer cells. The salt forms are represented by the structure of formula (I):

A-D.Y                                    (I)

wherein,

A denotes an amino acid comprising on its side chain at least one functional group selected from the group consisting of a carboxyl group, an amino group, a sulfhydryl group and a hydroxyl group;

D denotes a residue of a drug selected from the group consisting of a cytotoxic agent, a cytostatic agent and a chemotherapeutic agent, wherein D is attached to A through the side chain functional group of A; and Y is selected from the group consisting of: a pharmaceutically acceptable organic or inorganic acid or residue of an acid (i.e., the conjugate base of said acid), a pharmaceutically acceptable inorganic cation, a pharmaceutically acceptable organic amine; and an amino acid.

Pharmaceutical Salt

The term "pharmaceutical salt" as used herein refers to "pharmaceutically acceptable salts" of drug substances according to IUPAC conventions. Pharmaceutical salt is an inactive ingredient in a salt form combined with a drug. The term "pharmaceutically acceptable salt" as used herein, refers to salts of the compounds of the general formula (I), formula (II) and formula (III), e.g., compounds (1), (1A), (1B), (2), (3) or (4), or any other salt form encompassed by the generic formula, which are substantially non-toxic to living organisms. Typical pharmaceutically acceptable salts include those salts prepared by reaction of the compounds of the present invention with a pharmaceutically acceptable mineral, base, acid or salt as described herein. Acid salts are also known as acid addition salts.

Pharmaceutical salts such as are known in the art (Stahl and Wermuth, 2011, Handbook of pharmaceutical salts, second edition), the contents of which are hereby incorporated by reference in their entirety, are exemplified herein below in some non-limiting embodiments.

In the compounds of the present invention, the group Y represents the salt form. Y can be (or can be derived from) any pharmaceutically acceptable organic or inorganic acid or base, non-limiting examples of which are provided below:

(i) Acid Addition Salts:

In one embodiment, Y is a pharmaceutically acceptable organic or inorganic acid or residue of an acid, selected from the group consisting of acetic acid, hydrochloric acid, methanesulfonic acid, phosphoric acid, citric acid, lactic acid, succinic acid, tartaric acid, boric acid, benzoic acid, 2-(4-hydroxybenzoyl)-benzoic, toluenesulfonic acid, benzenesulfonic acid, ascorbic acid, sulfuric acid, maleic acid, formic acid, malonic acid, nicotinic acid, oxalic acid, camphorsulfonic acid, cyclamic acid, 2,2-dichloro-acetic acid, di(t-butyl)-naphthalenesulfonic acid, di(t-butyl)-naphthalenedisulfonic acid, dodecylsulfuric acid, ethane-1,2-disulfonic acid, ethanesulfonic acid, fumaric acid, galactaric (mucic) acid, gentisic acid, glucaric acid, gluconic acid, glycerophosphoric acid, hydrobromic acid, hydroiodic acid, 2-hydroxy-ethanesulfonic (isethionic) acid, 1-hydroxy-2-naphtoic acid, medronic (bisphosphonic) acid, methaphosphoric acid, methylboronic acid, naphthalene-1,5-disulfonic acid, naphthalene-2-sulfonic acid, nitric acid, orotic acid, 2-oxo-glutaric (ketoglutaric) acid, pamoic (embonic) acid, pyruvic acid, saccharinic acid, salicylic acid, 4-amino-salicylic acid, and thiocyanic acid. Each possibility represents a separate embodiment of the present invention.

In some currently preferred embodiments, Y is a pharmaceutically acceptable acid selected from the group consisting of acetic acid, hydrochloric acid, methanesulfonic acid, phosphoric acid, citric acid, lactic acid, succinic acid, tartaric acid, boric acid, benzoic acid, toluenesulfonic acid, benzenesulfonic acid, ascorbic acid, sulfuric acid, maleic acid, formic acid, malonic acid, nicotinic acid and oxalic acid. Each possibility represents a separate embodiment of the present invention.

Other embodiments of pharmaceutical acid salt forms can be created from acids including aceturic, 4-acetamido-benzoic, adipic, aminohippuric, 4-amino-salicylic, alginic, aspartic, boric, butyric, capric (decanoic), caproic (hexanoic), carbonic, camphoric, camphorsulfonic, caprylic (octanoic), cyclamic, cinnamic, 2,2-dichloro-acetic, di(t-butyl)-naphthalenesulfonic, di(t-butyl)-naphthalenedisulfonic, dehydroacetic, diatrizoic, dodecylsulfuric, ethane-1,2-disulfonic, edetic, ethanesulfonic, 2-ethyl-hexanoic, erythorbic, formic, fumaric, galactaric (mucic), gentisic, glucoheptanoic, gluconic, glucuronic, glutamic, glutaric, glycerophosphoric, glycolic, hippuric, hydrochloric, hydrobromic, hydroiodic, 2-(4-hydroxybenzoyl)-benzoic, 2-hydroxy-ethanesulfonic (isethionic), 1-hydroxy-2-naphtoic, isobutyric, lactic, lactobionic, lauric, iodoxamic, isostearic, maleic, malic, malonic, mandelic, medronic, methanesulfonic, methaphosphoric, methylboronic, myristic, naphthalene-1,5-disulfonic, naphthalene-2-sulfonic, nicotinic, oleic, oxalic, palmitic, pentetic, propionic, propanoic, pyroglutamic, pyruvic, phosphoric, sebacic, sorbic, stearic (octadecanoic), suberic, succinic, sulfuric, tartaric, thiazoximic, thiocyanic, toluenesulfonic, trifluoroacetic and undecylenic (undec-10-enoic) acids. Each possibility represents a separate embodiment of the present invention.

(ii) Basic Addition Salts:

In one embodiment, Y is a pharmaceutically acceptable organic or inorganic base or residue of a base, selected from the group consisting of alkali metals, alkaline earth metals, aluminum, zinc and ammonium.

In some currently preferred embodiments, Y is pharmaceutically acceptable inorganic cation selected from the group consisting of lithium, sodium, potassium, calcium, magnesium, aluminum, zinc and ammonium. Each possibility represents a separate embodiment of the present invention.

In other current preferred embodiment, Y is a pharmaceutically acceptable organic amine selected from the group consisting of ammonium, a primary amine, a secondary amine, a tertiary amine, a quaternary ammonium compound, an amino alcohol and an amino sugar. In some currently preferred embodiments, Y is an organic amine base selected from the group consisting of benethamine, benzathine, betaine, t-butylamine (erbumine), deanol, dicyclohexylamine, diethylamine, 2-diethylamino-ethanol, diethanolamine, ethanolamine, ethylenediamine, hydrabamine, morpholine, 4-(2-hydroxyethyl) morpholine, 1-(2-hydroxyethyl)-pyrrolidine (epolamine), imidazole, N-methylglucamine (meglumine), 4-phenylcyclohexylamine, piperazine, and tromethamine. Each possibility represents a separate embodiment of the present invention.

Other basic pharmaceutical salt forms can be created from bases including aluminum hydroxide, ammonia, arginine, benethamine, benzathine, betaine, t-butylamine (erbumine), calcium hydroxide, choline hydroxide, deanol, diethylamine, 2-diethylamino-ethanol, diethanolamine, ethanolamine, ethylenediamine, hydrabamine, 4-(2-hydroxyethyl) morpholine, 1-(2-hydroxyethyl)-pyrrolidine (epolamine), imidazole, lithium hydroxide, lysine, N-methylglucamine (meglumine), magnesium hydroxide, 4-phenylcyclohexylamine, piperazine, potassium hydroxide, sodium hydroxide, tromethamine, and zinc hydroxide. Each possibility represents a separate embodiment of the present invention.

As understood by a person of skill in the art, the aforementioned acids can react with a basic moiety (e.g., an amino group) on the amino acid-drug conjugate to form a salt. For example, when the acid is a carboxylic acid and the conjugate comprises a basic amine moiety, the salt may be represented by the structure R—COO$^-$ R'—NH$_3^+$. Similar acid-base reaction products may form with any of the other acids described herein.

(iii) Salts with Amino Acids

In other current preferred embodiment, Y is an amino acid capable of forming salt forms, such as arginine or lysine. Each possibility represents a separate embodiment of the present invention.

(iv) Other Salts

Other pharmaceutical salt forms can be created from salts including ammonium acetate, ammonium sulfate, calcium acetate, calcium carbonate, calcium chloride, calcium gluceptate, calcium lactate, calcium phosphate, calcium sulfate, edatate calcium disodium, edatate disodium, edatate sodium, iodine, magnesium carbonate, magnesium chloride, magnesium nitrate, magnesium sulfate, potassium acetate, potassium carbonate, potassium citrate, potassium metabisulfite, potassium phosphate, potassium sorbate, sodium acetate, sodium acid pyrophosphate, sodium alginate, sodium alkyl sulfate, sodium aminobenzoate, sodium ascorbate, sodium benzoate, sodium bicarbonate, sodium bisulfate, sodium bisulfate, sodium borate, sodium carbonate, sodium carragenate, sodium chlorate, sodium chloride, sodium citrate, sodium dithionate, sodium hypochloride, sodium iodide, sodium lactate, sodium metabisulfite, sodium phosphate, sodium pyrophosphate, sodium succinate, sodium sulfate, sodium sulfite, sodium tartarate, sodium thioglycolate, sodium thiosulfate, stannous chloride, zinc acetate, zinc chloride, and zinc sulfate. Each possibility represents a separate embodiment of the present invention.

Amino Acids (A)

According to one embodiment the amino acid (A) is an L configuration, D configuration or mixture thereof. Each possibility represents a separate embodiment of the present invention.

The amino acid A may be an α-amino acid, β-amino acid, γ-amino acid, δ-amino acid or ε-amino acid, with each possibility representing a separate embodiment of the present invention. Currently preferred amino acids are α-amino acids.

In some embodiments, the amino acid (A) is selected from the group consisting of aminoisobutyric acid (Aib), arginine (Arg), asparagine (Asn), aspartic acid (Asp), citrulline (Cit), cysteine (Cys), cystine, diaminobutanoic acid, diaminobutyric acid (Dab), diaminopropionic acid (Dpr), dihydroxyphenylalanine, dimethylarginine, glutamic acid (Glu), pyroglutamic acid (p-Glu), glutamine (Gln), histidine (His), 1-methyl-histidine, 3-methyl-histidine, homoserine (Hse), homocitrulline, hydroxyproline (Hyp), lysine (Lys), methyllysine, dimethyl lysine, trimethyl lysine, azidolysine, methionine (Met), methionine-sulfoxide, methionine-sulfone, ornithine (Orn), sarcosine (Sar), Selenocystein (Sec), serine (Ser), phosphor-serine, methyl-serine, aminoserine (Ams), thienylalanine (Thi), threonine (Thr), phospho-threonine, tryptophan (Trp), tyrosine (Tyr), methyl-tyrosine, phosphor-tyrosine, sulfo-tyrosine, α-aminosuberic acid, 3,5-diiodotyrosine, penicillamine (Pen), 4-ethylamine phenylglycine, 4-aminophenylglycine, 4-sulfophenylalanine, 4-aminophenylalanine and 2-amino-4[4-(2-amino)-pyrimidinyl]butanoic acid, 3-aminopropionic acid, 6-aminohexanoic acid (ε-Ahx), p-aminobenzoic acid, isonipecotic acid, statine (Sta), 2-aminobutyric acid (Abu) and 4-aminobutyric acid, α-aminoadipic acid (Aad), α-aminopimelic, γ-carboxy-glutamic acid, γ-hydroxy-glutamic acid, aminoglycine, and derivatives and analogs thereof. Each possibility represents a separate embodiment of the present invention.

In some embodiments, the amino acid (A) is selected from the group consisting of asparagine, aspartic acid, glutamine, glutamic acid, and derivatives and analogs thereof. In one currently preferred embodiment, the amino acid (A) is glutamic acid. In another currently preferred embodiment, the amino acid (A) is aspartic acid.

Drug (D)

The group D may be derived from any drug selected from the group consisting of a cytotoxic agent, a cytostatic agent and a chemotherapeutic agent. In some embodiments, the cytotoxic, cytostatic or chemotherapeutic agent D is the residue of a drug selected from the group consisting of a pyrimidine analog, a purine analog, an antifolate, hydroxyurea, an antimicrotubule agent, an alkylating agent, an antitumor antibiotic, a topoisomerase targeting agent, an antimetabolite, a DNA binding agent and a DNA antagonist.

In some embodiments, the cytotoxic, cytostatic or chemotherapeutic agent D is the residue of a pyrimidine analog selected from the group consisting of cytosine arabinoside (ara-C, cytarabine), gemcitabine, fluorouracil, 5-fluorodeoxyuridine, ftorafure, capecitabine, carmofure, BOF-A2, 5-chloro-2,4-dihydroxypyridine, decitabine, leflunomide, trifluridine, iodoxuridine, zidovudine, telbivudine, trimethoprim, fluorocytosine, deoxythymidine and 5-amino-6-nitro uracil. Each possibility represents a separate embodiment of the present invention.

In other embodiments, the cytotoxic, cytostatic or chemotherapeutic agent D is the residue of a purine analog selected from clofarabine, decarbazine, cladribine, mercaptopurine, nelarabine, pentostatine, thioguanine, gefitinib, azathiopurine, 8-azaguanine, immucillin-G, 2-fluoro-2'-deoxyadenosine, 9-beta-D-xylofuranosyl-adenine, 3-dexoxyguanine, 6-methyl-formycin A, 2-fluoroadenosine, 1-deaza-adenosine, N-ethyl-5-carboxamido-adenosine, 3'-oxo-adenosine, 2-amino-adenosine, 6-O-cyclomethyl-guanine, fludarabine, and 8-iodo-guanine. Each possibility represents a separate embodiment of the present invention.

In other embodiments, the cytotoxic, cytostatic or chemotherapeutic agent D is the residue of an anti-cancer drug selected from the group consisting of 2,4-dioxo-5-fluoropyrimidine (5-FU), fluorodeoxyuridine (5-FUDR), azacytidine (5-AZC), 6-mercaptopurine (6-MP), 6-thioguanine (6-TG), chlorodeoxyadenosine (2-CDA) and pentostatin (dCF). Each possibility represents a separate embodiment of the present invention.

In one currently preferred embodiment, the cytotoxic, cytostatic or chemotherapeutic agent D is the residue of cytarabine. In another currently preferred embodiment, the cytotoxic, cytostatic or chemotherapeutic agent D is the residue of gemcitabine.

The present invention also relates to an asparagine-drug conjugate wherein the cytotoxic, cytostatic or chemotherapeutic agent drug D is an antimetabolite, which can inhibit enzymes involved in the metabolism of asparagine. One important enzyme that can be inhibited by the asparagine-drug conjugate is asparagine synthetase, which is essential for asparagine synthesis in mammalian cells. Other enzymes involved in the metabolism of glycoproteins, especially those that have N-linked sugars connected to the asparagine amino acid in the protein including, but not limited, glucosidase I, glucosidase II, calnexin, and alpha-glucosyltransferase can be potentially inhibited by an asparagine-drug conjugate. N-glycosylation in N-glycan proteins occurs on asparagine at the consensus sequence Asn-X-Ser/Thr, and interference with glycosylation metabolism disrupts the folding and secretion of glycoproteins. Inhibition of glycosylation of essential glycoproteins will cause cell arrest and cell death.

An asparagine-drug conjugate can also affect the metabolism of other amino acids such as ornithine, since asparagine has been shown to be involved in membrane Na+/H+ antiport in ornithine decarboxylase induction (Fong and Law, 1988).

An asparagine-drug conjugate can undergo fast uptake by aspartate and glutamate transporters, which mediate delivery of glutamic/glutamine and aspartic/asparagine amino acids through the blood brain barrier (BBB), and can be applied as efficient drug delivery system to transport chemotherapeutic drugs to treat tumors of the CNS. It has been shown that cerebrospinal fluid (CSF) and plasma levels of asparagine are significantly lower in patients with primary and secondary tumors of the Central Nervous System (CNS), (Piek et al., 1987).

Hepatoma cancer cells have been shown to express a glutamine transporter, which shows a much higher rate of glutamine uptake in human hepatoma cells, and not in normal hepatocytes, thus indicating that glutamine-drug conjugate can be used for treatment of liver cancers.

As noted above, in the conjugates of the present invention, the drug reside (D) is attached to the amino acid (A) through the side chain functional group of (A). Some non-limiting embodiments of such conjugates are described below.

In specific embodiments, the compound comprises the amino acid aspartic acid or glutamic acid residue conjugated to a drug selected from the group consisting of purine analogs and pyrimidine analogs. In specific embodiments, the drug is selected from cytarabine and gemcitabine. In specific embodiments, the salt form of the amino acid-drug conjugate is an acid salt form selected from acetic acid and hydrochloric acid.

Without wishing to be bound to theory, the amino-acid conjugate salts of the present invention are transported into the cell via amino acid transporters thereby bypassing multi-drug resistance (MDR) mechanisms, and arrest cell growth or kill the cell from within.

According to some embodiments, the amino acid (A) is selected from the group consisting of aspartic acid and glutamic acid, and the compound is represented by the structure of formula (II) or (III)

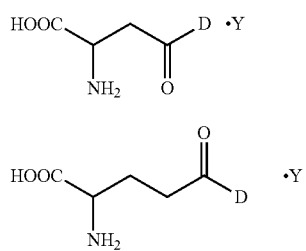

wherein D and Y are as defined above.

In a specific embodiment of formula (II), A is aspartic acid and D is the residue of cytarabine, and the compound is represented by the structure of formula (1):

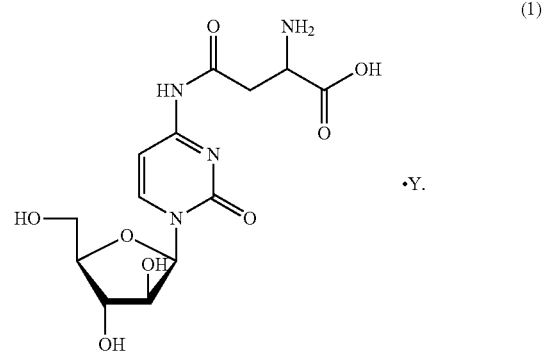

In one embodiment of formula (1), the compound is a salt with acetic acid (i.e., an acetate salt) which is represented by the structure of formula (1A):

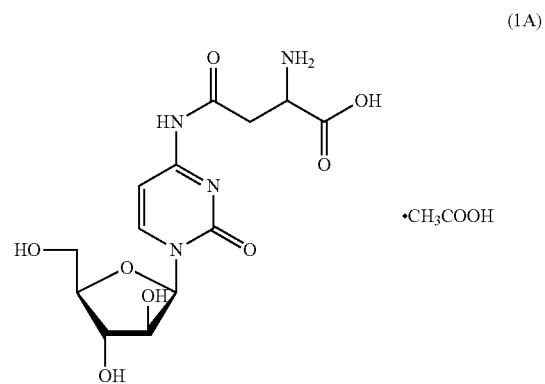

In another embodiment of formula (1), the compound is a salt with hydrochloric acid (i.e., a hydrochloride salt), which is represented by the structure of formula (1B):

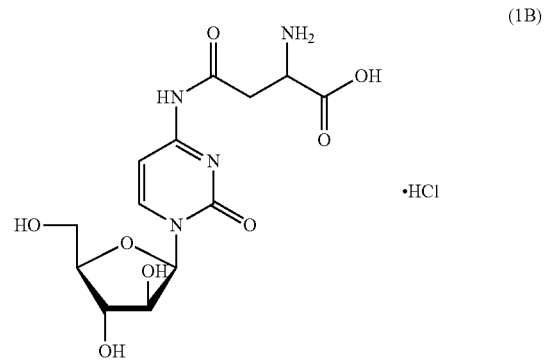

In another specific embodiment of formula (II), A is aspartic acid and D is the residue of gemcitabine, and the compound is represented by the structure of formula (2):

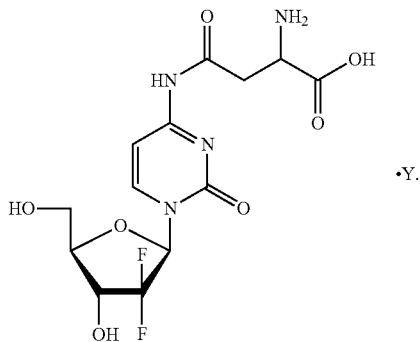

(2)

In a specific embodiment of formula (III), A is glutamic acid and D is the residue of cytarabine, and the compound is represented by the structure of formula (3):

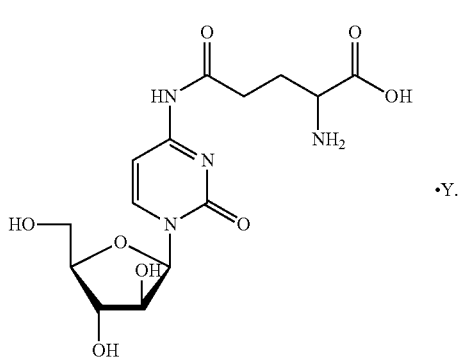

(3)

In another specific embodiment of formula (III), A is glutamic acid and D is the residue of gemcitabine, and the compound is represented by the structure of formula (4):

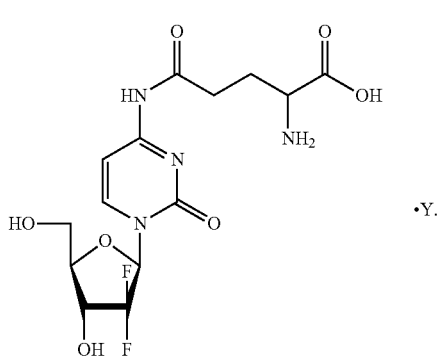

(4)

In any of the aforementioned compounds of formula (1), (2), (3) and (4), Y may be any of the options described above, may preferably be a pharmaceutically acceptable acid selected from the group consisting of acetic acid, hydrochloric acid, methanesulfonic acid, phosphoric acid, citric acid, lactic acid, succinic acid, tartaric acid, boric acid, benzoic acid, toluenesulfonic acid, benzenesulfonic acid, ascorbic acid, sulfuric acid, maleic acid, formic acid, malonic acid, nicotinic acid and oxalic acid.

Definitions

For convenience and clarity certain terms employed in the specification, examples and claims are described herein.

The term "residue of a drug" refers to a drug excluding the functional group that was used to attach the amino acid in forming the amino acid-drug conjugate A-D.

The term "residue of an acid" refers to the conjugate base of that acid. For example the conjugate base of hydrochloric acid (HCl) is chloride (Cl⁻). The conjugate base of acetic acid ($CH_3COOH$) is acetate ($CH_3COO^-$).

The term "drug" denotes any pharmacologically active agent capable of arresting cell growth, or inducing death of the hyperproliferative cell in which it is present and includes known cytotoxic, cytostatic, antiproliferative drugs such as are known in the art, as exemplified hereinabove. The classification of drugs herein is made for the sake of convenience only and is not intended to limit any component to a particular application or applications listed.

The term "cytotoxic agent" as used herein refers to an agent that is toxic to, damages and/or destroys cells, e.g. cancer cells. Chemotherapy by chemotherapeutic drugs is a form of cytotoxic therapy.

The term "cytostatic drug" as used herein refers to any substance that inhibits cell growth and division.

The term "chemotherapeutic agent" as used herein refers to a drug used in chemotherapy.

As used herein, "arresting cell growth" and "inducing death" of the hyperproliferative cell, e.g., neoplastic cell, refers to slowing, interrupting, arresting or stopping its growth and metastasis, and does not necessarily indicate a total elimination of the neoplastic growth.

The amino acids used in this invention are those, which are available commercially or are available by routine synthetic methods. Natural coded amino acids and their derivatives are represented by three-letter codes according to IUPAC conventions. When there is no indication, either the L or the D isomer may be used. The D isomers are indicated by "D" before the residue abbreviation.

As used herein, the term "stereoisomer" refers to a compound made up of the same atoms bonded by the same bonds but having different three-dimensional structures, which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers, which are not enantiomers. In addition, two diastereomers, which have a different configuration at only one chiral center are referred to herein as "epimers". The terms "racemate", "racemic mixture" or "racemic modification" refer to a mixture of equal parts of enantiomers. The present invention includes enantiomers of the compounds having general formula (I), (II) and (III), and the specific compounds described herein.

Synthetic Methods

In the conjugate according to the present invention, the drug is covalently attached to the amino acid or amino acid analog. The skilled artisan will be able to optimize the appropriate linkage and position of the drug moiety within the compound. Various concerns should be taken into consideration to guide the artisan in this decision, such as selection of the specific drug, selection of the derivatives, selection of the position of attachment to the drug species, and requirements concerning host intracellular enzymes for drug activation.

Thus, in accordance with another aspect, the present invention provides a method for preparing a pharmaceutically acceptable salt represented by the structure of formula I, comprising the step of (a) reacting a compound of the formula (IV):

(A-D)-(P)$_n$                                 (IV)

wherein A and D are as defined above,
n is an integer of 1-6; and
each P is independently at each occurrence a protecting group; wherein each P is attached to any functional group available for protection on the amino acid (A), the drug residue (D) or to both the amino acid (A) and the drug residue (D);

with a reagent capable of removing the protecting group(s) P; and (b) adding a reagent capable of introducing the group Y, so as to generate a salt represented by the formula:

A-D.Y                                                (I)

wherein Y is as defined above.

As mentioned above, it has now been unexpectedly discovered that the salts of the present invention can be prepared by deprotecting a precursor compound containing one or more protecting groups (P) using the same reagent that ultimately forms the salt. Thus, according to the principles of the present invention, the reagent capable of introducing the group Y can simultaneously remove the protecting group(s) P and generate the salt of formula (I) in one step, thereby obviating an intermediate step of deprotection prior to salt formation, which ultimately leads to higher purity pharmaceutical product. Specifically, use of TFA for deprotection of BOC is avoided, leading to the generation of a salt of the conjugate of the present invention represented by formula I, which salt is devoid or free of toxic TFA. Specific embodiments of this process are described herein below. The compounds described herein comprise a pharmaceutical salt form of an anti-cancer drug conjugated to an amino acid or derivatives or analogs of amino acids. The compounds of the present invention can be readily prepared from amino acids by methods familiar to one with skill in the art. For example, the conjugates or their precursors may be prepared in accordance with the methods disclosed in International Patent Application Publication No. WO 2005/072061 and U.S. Pat. No. 7,989,188, the contents of which are incorporated by reference herein. The conjugates (or their protected precursors) can then react with a reagent capable of introducing the group Y (e.g., the reagent is an acid or base) so as to form the compounds of formula (I). Additional methods useful to prepare the compounds of the invention are, e.g., the methods described in International Patent Application Publication Nos WO96/30036 and WO97/36480, and U.S. Pat. Nos. 5,643,957 and 5,650,386, among others. For example, the compounds may be prepared by reacting the single amino acid with the appropriate catalyzing agent, which reacts with a free moiety present in the amino acid and conjugating it to a free moiety on the drug to form an ester or amide. Protecting groups may be used to avoid unwanted side reactions as would be known to those skilled in the art. The contents of each of the above references are incorporated by reference herein.

For example, for the purpose of illustration and not for limitation, conjugates of formula (II) (Aspartic acid-drug conjugates) or formula (III) (Glutamic acid-drug conjugates) can be prepared by reacting Aspartic acid or Glutamic acid which are protected on the amine and alpha carboxyl (compound (i) and (iii) in Schemes 1A and 1B), with the drug or an activated and/or protected derivative thereof in the presence of a coupling reagent, followed by deprotection. The drug (D) may be unprotected or protected at any available functional group (e.g., OH, NH$_2$, SH, carboxyl etc.), with any one of the protecting groups described herein. Exemplary processes are represented in Schemes 1A and 1B:

Scheme 1A

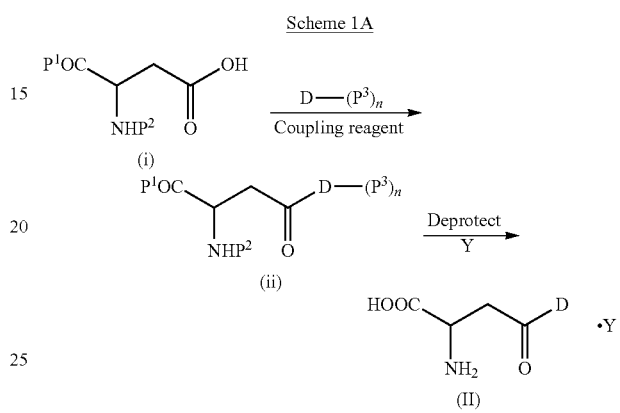

Scheme 1B

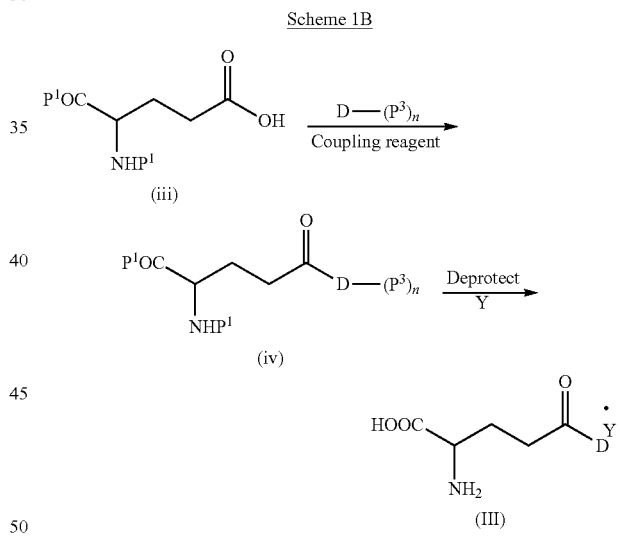

wherein P$^1$ is a carboxy protecting group, P$^2$ is an amino protecting group, P$^3$ is a protecting group located on one or more functional groups on the drug D, and n is 0, 1, 2 or 3. Depending on the number of functional groups on the drug, n could also be 4, 5, 6, etc.

In one embodiment, the drug is cytarabine. In other embodiments the drug is protected-cytarabine, comprising protecting groups on its 2', 3' and/or 5' hydroxyl moieties, such as triphenylmethyl-cytarabine (CAS 7075-13-0), benzoyl-cytarabine (CAS 34270-10-5), admantoyl-cytarabine (CAS 23113-01-1), and trimethylsilyl-cytarabine. In other embodiments, the drug is gemcitabine. In other embodiments the drug is a protected-gemcitabine comprising protecting groups on its 3' and/or 5' hydroxyl moieties, such as triphenylmethyl-gemcitabine (CAS 1642862-24-5).

A non-limiting example of a protected drug is a protected Cytarabine, wherein at least one of the 2', 3' or 5' hydroxyls are protected with a group $P^3$ as defined above. In one non-limited embodiment depicted below for the purpose of illustration, the compound is represented by formula E, wherein each of the 2', 3' or 5' hydroxyls are protected with a group $P^3$.

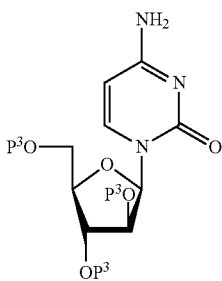

E

In other embodiments, only the 5'—OH group is protected, while the 2' and 3' hydroxyls are unprotected.

A another non-limiting example of a protected drug is a protected Gemcitabine, wherein at least one of the 3' or 5' hydroxyls are protected with a group $P^3$ as defined above. In one non-limited embodiment depicted below for the purpose of illustration, the compound is represented by formula F, wherein each of the 3' or 5' hydroxyls are protected with a group $P^3$.

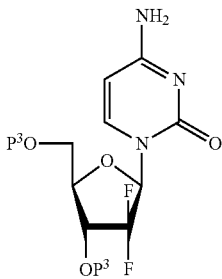

F

In other embodiments, only the 5'—OH group is protected, while the 3' hydroxyl is unprotected.

In one embodiment, designated herein as "Route A", the deprotection step is conducted in the presence of trifluoroacetic acid (TFA), followed by reaction an acid to introduce the group Y. In accordance with this embodiment, the present invention provides a pharmaceutically acceptable salt preferably comprising less than about 5% TFA as a residual impurity, preferably less than about 1% TFA, more preferably less than about 0.1% TFA. Most preferably, the salt of the present invention is substantially devoid of TFA as an impurity.

In another embodiment, designated herein as "Route B", the deprotection step is conducted directly with the reagent capable of introducing the group Y (i.e., an acid) to directly afford the salt of the present invention. In accordance with this embodiment, the protecting groups are removed simultaneously with introduction of the group Y, and the resulting pharmaceutically acceptable salt is completely devoid of TFA as an impurity.

Protecting Groups (P)

Precursors of compound (I) can include one or more protecting groups (P), exemplified above as $P^1$, $P^2$ and $P^3$, which can be any protecting group known to a person of skill in the art. The term "protecting group" refers to chemical residues used to block reactive sites during chemical synthesis, that enable chemical reaction to be carried out selectively at one reaction site in a multifunctional compound, other reactive sites must be temporarily blocked. The residues used to block these reactive sites called protecting groups.

The protecting group can be a hydroxyl protecting group, an amino protecting group, a carboxy protecting group, etc. As used herein, the term "OH protecting group" or "hydroxy protecting group" refers to a readily cleavable group bonded to hydroxyl groups. As used herein, the term "NH protecting group" or "amino protecting group" refers to a readily cleavable group bonded to amino groups. As used herein, the term "carboxy protecting group" refers to a readily cleavable group bonded to carboxy groups.

According to one embodiment, the protecting group P is selected from group of acetamidomethyl (Acm), acetyl (Ac), acetonide, adamantyloxy (AdaO), alfa-allyl (OAll), Alloc, benzoyl (Bz), benzyl (Bzl), benzyloxy (BzlO), benzyloxycarbonyl (Z), benzyloxymethyl (Bom), bis-dimethylamino ($NMe_2$), 2-bromobenzyloxycarbonyl (2-Br—Z), t-butoxy (tBuO), t-butoxycarbonyl (Boc), t-butoxymethyl (Bum), t-butyl (tBu), t-butylthio (tButhio), 2-chlorobenzyloxycarbonyl (2-Cl—Z), 2-chlorotrityl (2-Cl-Trt), cyclohexyloxy (cHxO), 1-cyclopropyl-1-methyl-ethyl (Dmcp), 2,6-dichlorobenzyl, 4,4'-dimethoxybenzhydryl (Mbh), 1-(4,4-dimethyl-2,6-dioxo-cyclohexylidene)-3-methylbutyl (ivDde), 4 {N-[1-(4,4-dimethyl-2,6-dioxo-cyclohexylidene)-3-methyl-butyl]-amino}benzyloxy (ODmab), 2,4-dinitrophenyl (Dnp), fluorenylmethoxycarbonyl (Fmoc), formyl (For), Mesitylene-2-sulfonyl (Mts), 4-methoxybenzyl, 4-methoxy-2,3,6-trimethylbenzenesulfonyl (Mtr), 4-methoxytrityl (Mmt), 4-methybenzyl (MeBzl), 3-methylpent-3-yl (Mpe), 1-methyl-1-phenyl-ethyl (PhiPr), Methyl, 4-methyltrityl (Mtt), 3-nitro-2-pyridinesulfenyl (Npys), 2,2,4,6,7-pentamethyl-dihydrobenzofurane-5-sulfonyl (Pbf), 2,2,5,6,8-pentamethyl-chromane-6-sulfonyl (Pmc), tosyl (Tos), trifluoroacetyl (Tfa), trimethylacetamidomethyl (Tacm), Triphenylmethyl (trityl,Trt) and Xanthyl (Xan). Each possibility represents a separate embodiment of the present invention.

A non-limiting example of a hydroxyl protecting group is an acyl group (COR wherein R=alkyl, aryl, etc.). A currently preferred acyl group is an acetyl group (i.e., OR'=acetate, OAc). Another example of a hydroxy protecting group is a silyl group, which can be substituted with alkyl (trialkylsilyl), with an aryl (triarylsilyl) or a combination thereof (e.g., dialkylphenylsilyl). A preferred example of a silyl protecting group is trimethylsilyl (TMS) or di-t-butyldimethyl silyl (TBDMS), Triisopropylsilyl (TIPS), Triethylsilyl (TES). Other examples of hydroxy protecting groups include, for example, $C_1$-$C_4$ alkyl, —CO—($C_1$-$C_6$ alkyl), —$SO_2$—($C_1$-$C_6$ alkyl), —$SO_2$-aryl, —CO—Ar in which Ar is an aryl group as defined above, and —CO—($C_1$-$C_6$ alkyl)Ar (e.g., a carboxybenzyl (Bz) group).

Examples of amino-protecting groups include t-butoxycarbonyl (BOC), benzyloxycarbonyl, acetyl, phenylcarbonyl, or a silyl group, which can be substituted with alkyl (trialkylsilyl), with an aryl (triarylsilyl) or a combination thereof (e.g., dialkylphenylsilyl), e.g., trimethylsilyl (TMS) or t-butyldimethyl silyl (TBDMS). Other examples of hydroxy protecting groups include, for example, $C_1$-$C_4$ alkyl (e.g., methyl, ethyl, propyl, butyl and the like), —CH$_2$Ph (benzyl or bzl), allyl (All), (allyl)-CO—(C$_1$-C$_6$ alkyl), —SO$_2$—(C$_1$-C$_6$ alkyl), —SO$_2$-aryl, —CO—Ar in which Ar is an aryl group as defined above, and —CO—(C$_1$-C$_6$ alkyl)Ar (e.g., a carboxybenzyl (Bz) group). Other examples of hydroxy protecting groups include acid sensitive protecting groups such as tetrahydropyranyl (THP), methoxymethyl (MOM), triphenylmethyl (Trityl) and dimethoxy trityl (DMT). Each possibility represents a separate embodiment of the present invention.

Representative carboxy-protecting groups include, but are not limited to, methyl, ethyl, t-butyl, benzyl (Bn), p-methoxybenzyl (PMB), 9-fluorenylmethyl (Fm), trimethylsilyl (TMS), t-butyldimethylsilyl (TBDMS), diphenylmethyl (benzhydryl, DPM) and the like. Protecting groups may be removed by deprotecting agents which, according to the principles of the present invention, are preferably the same as the pharmaceutical salt moiety. In certain embodiments the pharmaceutical acids suitable for removal of acid labile protecting groups are: acetic acid, aceturic, 4-acetamido-benzoic, adipic, aminohippuric, 4-amino-salicylic, ascorbic, alginic, aspartic, benzenesulfonic, benzoic, boric, butyric, capric (decanoic), caproic (hexanoic), carbonic, citric, camphoric, camphorsulfonic, caprylic (octanoic), cyclamic, cinnamic, 2,2-dichloro-acetic, di(t-butyl)-naphthalenesulfonic, di(t-butyl)-naphthalenedisulfonic, dehydroacetic, diatrizoic, dodecylsulfuric, ethane-1,2-disulfonic, edetic, ethanesulfonic, 2-ethyl-hexanoic, erythorbic, formic, fumaric, galactaric (mucic), gentisic, glucaric, glucoheptanoic, gluconic, glucuronic, glutamic, glutaric, glycerophosphoric, glycolic, hippuric, hydrochloric, hydrobromic, hydroiodic, 2-(4-hydroxybenzoyl)-benzoic, 2-hydroxy-ethanesulfonic (isethionic), 1-hydroxy-2-naptoic, isobutyric, lactic, lactobionic, lauric, iodoxamic, isostearic, maleic, malic, malonic, mandelic, medronic, methanesulfonic, methaphosphoric, methylboronic, myristic, naphthalene-1,5-disulfonic, naphthalene-2-sulfonic, nicotinic, nitric, oleic, orotic, oxalic, 2-oxo-glutaric (ketoglutaric), palmitic, pamoic (embonic), pentetic, propionic, propanoic, pyroglutamic, pyruvic, phosphoric, saccharine, salicylic, sebacic, sorbic, stearic (octadecanoic), suberic, succinic, sulfuric, tartaric, thiazoximic, thiocyanic, toluenesulfonic, trifluoroacetic and undecylenic (undec-10-enoic) acids. Each possibility represents a separate embodiment of the present invention.

In specific embodiments, the pharmaceutically acceptable acid that reacts with the precursor compound of formula (IV) and removes the protecting group is selected from the group consisting of acetic acid, methanesulfonic acid, hydrochloric acid, phosphoric acid, citric acid, lactic acid, succinic acid, tartaric acid, boric acid, benzoic acid, toluenesulfonic acid, benzenesulfonic acid, ascorbic acid, sulfuric acid, maleic acid, formic acid, malonic acid, nicotinic acid and oxalic acid. In accordance with such embodiments, the resulting salt is selected from the group consisting of acetate, hydrochloride, methanesulfonate, phosphate, citrate, lactate, succinate, tartarate, borate, benzoate, toluenesulfonate, benzensulfonate, ascorbate, sulfate, maleate, formate, malonate, nicotinate and oxalate. Each possibility represents a separate embodiment of the present invention.

In certain embodiments the pharmaceutical bases suitable for removal of base labile protecting groups are: aluminum hydroxide, ammonia, arginine, benethamine, benzathine, betaine, t-butylamine (erbumine), calcium hydroxide, choline hydroxide, deanol, diethylamine, 2-diethylamino-ethanol, diethanolamine, ethanolamine, ethylenediamine, hydrabamine, 4-(2-hydroxyethyl) morpholine, 1-(2-hydroxyethyl)-pyrrolidine (epolamine), imidazole, lithium hydroxide, lysine, N-methylglucamine (meglumine), magnesium hydroxide, 4-phenylcyclohexylamine, piperazine, potassium hydroxide, sodium hydroxide, tromethamine, and zinc hydroxide. Each possibility represents a separate embodiment of the present invention.

In other embodiments, H$_2$ Pd/C may be used as a deprotecting agent when the protecting group is, e.g., benzyl.

Precursor compounds containing protecting groups may generally be described in Schemes 1A and 1B hereinabove.

In specific embodiments, the precursor is Boc-Asp(Cytarabine)-OtBu (formula A), whereas the protecting groups are removable by an acid to give Asp(Cytarabine).Y (formula 1), whereas Y is an acid salt form of a pharmaceutical acid.

In specific embodiments, the precursor is Boc-Asp (Gemcitabine)-OtBu (formula B), whereas the protecting groups are removable by an acid to give Asp(Gemcitabine).Y (formula 2), whereas Y is an acid salt form of a pharmaceutical acid.

In other specific embodiments, the precursor is Boc-Glu (Cytarabine)-OtBu (formula C), whereas the protecting groups are removable by an acid to give Glu(Cytarabine).Y (formula 3), whereas Y is an acid salt form of a pharmaceutical acid.

In other specific embodiments, the precursor is Boc-Glu (Gemcitabine)-OtBu (formula D), whereas the protecting groups are removable by an acid to give Glu(Gemcitabine).Y (formula 4), whereas Y is an acid salt form of a pharmaceutical acid. Other suitable protecting groups are described, e.g., in Wuts and Greene, 2007, "Greene's protective groups in organic synthesis", Fourth edition, the contents of which are incorporated by reference herein.

While it is preferred that the protecting group be removed by a pharmaceutical salt creating compound, the present invention is not limited to such embodiments. It is apparent to a person of skill in the art that the protecting group can be removed by other deprotecting agents, and the salt form of the drug may be generated in a separate, subsequent step.

The drug may be used as is, or as an activated or protected derivative thereof. For example, one embodiment of the present invention includes the use of cytarabine or gemcitabine that are protected on the hydroxyl groups of the sugar moieties (C2, C3 and/or C5) so as to prevent or minimize formation of a di-amino acid-Cytarabine or di-amino acid-Gemcitabine byproduct (i.e., a second amino acid attaching to the 5'-OH of the arabinose moiety). The protecting group on the sugar moiety can be any one of the protecting groups described above, and they can be removed with the appropriate deprotection agent as described herein.

The principles that apply to the selection of the organic/amino acid attachment site, protecting groups and pharmaceutical salt form etc., will be detailed herein for exemplary compounds. The principles may be generalized as follows:

a) Selection of the organic acid/amino acid or amino acid derivative or analog: aspartate/asparagine and glutamate/glutamine and any of their derivatives or analogs that can undergo rapid uptake by malignant or cancer cells are suitable, as is other organic acids that improve drug solubility, stability, bioavailability and patient compliance;

b) Selection of the protecting groups of the organic/amino acid: the groups may be selected from protecting groups suitable for the chemically functional groups on the organic acid/amino acid that can be removed by a compound that creates a pharmaceutical salt, as is other removable protecting groups;

c) Selection of the drug: the drug can be selected from anti-proliferative agents, cytotoxic agents and cytostatic agents;

d) Selection of the protecting groups of the drug: the groups may be selected from protecting groups suitable for the chemically functional groups on the drug that can be removed by a compound that creates a pharmaceutical salt, as is other removable protecting groups;

e) Selection of the reaction conditions for the conjugation of the drug to the organic acid: The optimal solvents, catalysts, additives and the time and temperature of the various reaction steps.

f) Selection of the conditions for removal of the protecting groups: by a pharmaceutical salt or other compound suitable for removing protecting groups and scavengers as known by skilled in the art (Wuts and Greene, 2007).

g) Selection of the pharmaceutical salt: the salt can be selected from a mineral, an acid additional salt, a base salt and a combination thereof.

h) Selection of the conditions for pharmaceutical salt creation: The optimal solvents/anti-solvents, concentrations and the time and temperature of the reaction.

The compounds and conditions for the conjugation reaction are exemplified but not limited by the following components:

Solvents: dimethylformamide (DMF), dimethylacetamide (DMA), ethanol, diethyl-ether, ethylacetate dimethylsulfoxide (DMSO), dichloromethane (DCM), dichloroethane (DCE), heptane, hexane, pyridine, 2-propanol, methanol, tert-butylmethylether, N-methylpyrrolidone (NMP), tetrahydrofuran (THF) trifluoroethanol (TFE), water and combination thereof;

Catalysts/coupling reagents: BOP (Benzotriazole-1-yl-oxy-tris-(dimethylamino)-phosphonium hexafluorophosphate), CDI (N,N'-carbonyldiimidazole), COMU (1-[(1-(Cyano-2-ethoxy-2-oxoethylideneaminooxy) dimethylaminomorpholino)] uronium hexafluorophosphate), DCC (N,N'-dicyclohexylcarbodiimide), DIC (N,N'-diisopropylcarbodiimide), EDC (1-ethyl-3-(3-dimethylaminopropyl) carbodiimide), DEPBT (3-(Diethoxy-phosphoryloxy)-1,2,3-benzo[d]triazin-4(3H)-one), HATU, HBTU (2-(1H-Benzotriazole-1-yl)-1,1,3,3-tetramethyluronium hexafluorophosphate), HCTU (O -(1H-6-Chlorobenzotriazole-1-yl)-1,1,3,3-tetramethyluronium hexafluorophosphate), MSNT (1-(Mesitylene-2-sulfonyl)-3-nitro-1H-1,2,4-triazole), PyBOP (Benzotriazole-1-yl-oxy-tris-pyrrolidino-phosphonium hexafluorophosphate), PyBroP (Bromo-tris-pyrrolidino-phosphonium hexafluorophosphate), TBTU (2-(1H-Benzotriazole-1-yl)-1,1,3,3-tetramethylaminium tetrafluoroborate), TFFH (Tetramethylfluoroformamidinium hexafluorophosphate), TOTU (O-[(ethoxycarbonyl)cyanomethyleneamino]-N,N,N',N',-tetramethyluronium);

Additives: DIPEA (diisopropylethylamine), DMAP (dimethylaminopyridine), pyridine, triethylamine, HOAt (N-hydroxy-9-azabenzotriazole), HOBt (N-hydroxybenzotriazole), Oxyma pure, NaclO$_4$, LiCl, KSCN and Triton.

Reaction temperatures of about 0° C. to about 80° C., preferably about 4° C. to about 25° C.;

Reaction times of about 3 minutes to about 72 hours, preferably about 3 to about 24 hours;

The compounds and conditions for the removal of protection groups are exemplified, but not limited by, the following components:

Pharmaceutical salts: including pharmaceutically acceptable mineral, base, acid or salt; the preferable acid and salt for removing protecting groups have a pKa≤3 and the preferable base and salt have a pKa>9.

Preferable acid for removing protecting groups having a pKa≤3 is selected from the group consisting of: benzenesulfonic, camphorsulfonic, cyclamic, 2,2-dichloro-acetic, di(t-butyl)-naphthalenesulfonic, di(t-butyl)-naphthalenedisulfonic, dodecylsulfuric, ethane-1,2-disulfonic, ethanesulfonic, fumaric, galactaric (mucic), gentisic, glucaric, gluconic, glycerophosphoric, hydrochloric, hydrobromic, hydroiodic, 2-hydroxy-ethanesulfonic (isethionic), 1-hydroxy-2-naphtoic, maleic, malonic, medronic (bisphosphonic), methanesulfonic, methaphosphoric, methylboronic, naphthalene-1, 5-disulfonic, naphthalene-2-sulfonic, nitric, orotic, oxalic, 2-oxo-glutaric (ketoglutaric), pamoic (embonic), pyruvic, phosphoric, saccharine, salicylic, sulfuric, tartaric, thiocyanic, toluenesulfonic and trifluoroacetic acid.

Other protecting group removing compounds including but not limited to: TMSBr, HBF$_4$, HF, piperidine, Pd(Ph$_3$P)$_4$, NH$_2$NH$_2$, I$_2$, and compounds of Tl, Hg, Ag, and Pd;

Scavengers: H$_2$O, TIS, TES, EDT, m-cresol, thioanisol, anisol, phenol;

Temperatures of −20° C. to 80° C., preferably 0° C. to 25° C.;

Times of 1 minute to 24 hours, preferably 1-3 hours;

The compounds and conditions for the pharmaceutical salt creation are selected from:

Solvents for dissolving the compound with the pharmaceutical acid: H$_2$O, dioxane, ethylacetate, methanol, ethanol, isopropanol, DMSO, tetrahydroforan (THF) and trifluoroethanol (TFE), or any combination thereof. In one currently preferred embodiment, the solvent is H$_2$O. In another currently preferred embodiment, the solvent is dioxane;

Anti-solvent for precipitating the product indicated in formula (I): diethyl-ether, t-butyl-methyl-ether (tBME), hexane, heptane, DCM.

Molar ratio of 1:1 to 1:30 of compound to pharmaceutical salt, preferably from 1:1.1 to 1:3, at room temperature (25° C.), incubated for 1 hour.

This invention further discloses hydrates of the pharmaceutically acceptable salts of general formula (I).

In one particular embodiment, the pharmaceutically acceptable acid is HCl and the solvent used is H$_2$O or dioxane. It has been unexpectedly been found that when dioxane/HCl is used, the product precipitates during the deprotection reaction, and there is no need for a separate precipitation step.

Pharmaceutical Compositions

The present invention further provides pharmaceutical compositions comprising at least one of the compounds of the present invention and one or more pharmaceutically acceptable excipients or diluents.

The compositions comprising the compounds of the present invention have utility in the delivery of active agents to selected biological systems and in an increased or improved bioavailability of the active agent compared to administration of the active agent without the delivery agent. Delivery can be improved by delivering more active agent over a period of time, or in delivering active agent in a particular time period (such as to effect quicker or delayed delivery) or over a period of time (such as sustained delivery).

Pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes.

As used herein a "pharmaceutical composition" refers to a preparation of one or more of the compounds described herein, or physiologically acceptable salts or solvents thereof, with other chemical components such as physiologically suitable carriers and excipients. The purpose of a pharmaceutical composition is to facilitate administration of a compound to a subject.

The pharmaceutical compositions of the invention may be administered by any suitable administration route selected from the group consisting of parenteral and oral administration routes. According to some embodiments, the route of administration is via parenteral administration. In various embodiments, the route of administration is intravenous, intraarterial, intramuscular, subcutaneous, intraperitoneal, intracerebral, intracerebroventricular, intrathecal or intradermal administration route. For example, the pharmaceutical compositions can be administered systemically, for example, by intravenous (i.v.) or intraperitoneal (i.p.) injection or infusion. According to a certain embodiment, the pharmaceutical composition is administered by intravenous infusion for 30 minutes to 2 hours, such as for 1 hour. The compositions of the invention may be administered locally and may further comprise an additional active agent and/or excipient.

Pharmaceutical compositions for use in accordance with the present invention thus may be formulated in conventional manner using one or more physiologically acceptable carriers comprising excipients and auxiliaries, which facilitate processing of the active compounds into preparations which, can be used pharmaceutically. Proper formulation is dependent upon the route of administration chosen.

For injection, the compounds of the invention may be formulated in aqueous solutions, preferably in physiologically compatible buffers such as Hank's or Ringer's solution or physiological saline buffer. For transmucosal and transdermal administration, penetrants appropriate to the barrier to be permeated may be used in the formulation. Such penetrants, including for example DMSO or polyethylene glycol, are known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar or alginic acid or a salt thereof such as sodium alginate.

In addition, enteric coating is useful as it is desirable to prevent exposure of the compounds of the invention to the gastric environment.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers.

In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the active compound for use according to the present invention are conveniently delivered in the form of an aerosol spray presentation from a pressurized pack or a nebulizer with the use of a suitable propellant, e. g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e. g., gelatin for use in an inhaler or insufflator may be formulated containing a powder mix of the peptide and a suitable powder base such as lactose or starch.

Pharmaceutical compositions for parenteral administration include aqueous solutions of the active ingredients in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the compounds, to allow for the preparation of highly concentrated solutions.

The active compounds of the present invention may also be formulated in rectal compositions such as suppositories or retention enemas, using, e.g., conventional suppository bases such as cocoa butter or other glycerides.

Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on many factors including the subject being treated, the severity of the affliction, the manner of administration, the judgment of the prescribing physician.

According to a certain embodiment, the formulations of the pharmaceutically acceptable salts of the invention are provided as an aqueous isotonic solution having osmolarity of about 300 mOsm and a pH of 4-8. Thus, the pharmaceutically acceptable carrier of the compound of the invention can be a buffered saline solution, a buffered dextrose solution, or a buffered glycerol solution having osmolarity of about 300 mOsm and a pH of 4-8.

In other embodiment, the buffer solution can be a pharmaceutically acceptable mono-ionic buffer system or a polyionic buffer system having an ionization pK in the range of 4-8.

Various buffers having a pK of 4-8 can be employed for adjusting the pH of the solution containing the pharmaceutically acceptable salt of the present invention such as, for example, ACES (N-(acetamido)-2-aminoethansulfonic acid); Acetate; N-(2-acetamido)-2-iminodiacetic acid; BES (N,N-bis[2-hydroxyethyl]-2-aminoethansulfonic acid); Bicine (2-(Bis(2-hydroxyethyl)amino)acetic acid); Bis-Tris methane (2-[Bis(2-hydroxyethyl)amino]-2-(hydroxymethyl)propane-1,3-diol); Bis-Tris propane (1,3-bis(tris(hydroxymethyl)methylamino)propane); Carbonate; Citrate; 3,3-dimethyl glutarate; DIPSO (3-[N, N-bis(2-hydroxyethyl)amino]-2-hydroxypropansulfonic acid); N-ethylmorpholine; Glycerol-2-phosphate; Glycine; Glycine-amid; HEPBS (N-(2-hydroxyethyl)piperazin-N'-4-buthanesulfonic acid); HEPES (N-(2-hydroxyethyl)piperazin-N'-2-ethanesulfonic acid); HEPPS (N-(2-hydroxyethyl)piperazin-N'-(3-propanesulfonic acid)); HEPPSO (N-(2-hydroxyethyl)piperazin-N'-(2-hydroxypropanesulfonic acid); Histidine; Hydrazine; Imidazole; Maleate; 2-methylimidazole; MES (2-(N-morpholino)ethanesulfonic acid); MOBS (4-(N-morpholino)-butansulfonic acid); MOPS (3-(N-morpholino)-propanesulfonic acid; MOPSO (3-(N-morpholino)-2-hydroypropanesulfonic acid); Oxalate; Phosphate; Piperazine; PIPES (1,4-Piperazine-diethanesulfonic acid); POPSO (Piperazine-N,N'-bis(2-hydroxypropanesulfonic acid)); Succinate; Sulfite; TAPS (3-[[1,3-dihydroxy-2-(hydroxymethyl)propan-2-yl]amino]propane-1-sulfonic acid); TAPSO (3-[[1,3-dihydroxy-2-(hydroxymethyl)propan-2-yl]amino]-2-hydroxypropane-1-sulfonic acid); Tartaric acid; TES (2-[[1, 3-dihydroxy-2-(hydroxymethyl)propan-2-yl]amino] ethanesulfonic acid); THAM (Tris) (2-Amino-2-hydroxymethyl-propane-1,3-diol); and Tricine (N-(2-Hydroxy-1,1-bis(hydroxymethyl)ethyl)glycine).

According to some embodiments, the buffer is a sulfonic acid derivative buffer including, but not limited to, ACES, BES, DIPSO, HEPBS, HEPES, HEPPS, HEPPSO, MES, MOBS, MOPS, MOPSO, PIPES, POPSO, Sulfite, TAPS, TAPSO, and TES buffer.

According to additional embodiments, the buffer is a carboxylic acid derivative buffer including, but not limited to, Acetate, N-(2-acetamido)-2-iminodiacetic acid, 2-(Bis(2-hydroxyethyl)amino)acetic acid, Carbonate, Citrate, 3,3-dimethyl glutarate, Lactate, Maleate, Oxalate, Succinate, and Tartaric acid buffer.

According to further embodiments, the buffer is an amino acid derivative buffer including, but not limited to, Bicine, Glycine, Glycine-amid, Histidine, and Tricine buffer.

According to yet further embodiments, the buffer is a phosphoric acid derivative buffer including, but not limited to, Glycerol-2-phosphate and phosphate buffer.

Alternatively, the buffered saline formulation can be, for example, Hank's balanced salt solution, Earle's balanced salt solution, Gey's balanced salt solution, HEPES buffered saline, phosphate buffered saline, Plasma-lyte, Ringer's solution, Ringer Acetate, Ringer lactate, Saline citrate, or Tris buffered saline.

The buffered dextrose solution formulation can be, for example, acid-citrate-dextrose solution or Elliott's B solution.

According to exemplary embodiments, the solutions for injection is Plasma-Lyte A or Compound Sodium Lactate purchased from Baxter.

Therapeutic Use

The compounds of the present invention are useful in arresting cell growth, or inducing death of the hyperproliferative cell in which it is present and includes known cytotoxic, cytostatic, antiproliferative drugs such as are known in the art. As such, the compounds of the present invention are useful in the treatment and prevention of a variety of cancers, as well as pre-treatment prior to a bone marrow transplant.

Thus, in some embodiments, the present invention provides a method of treating a cancer including metastases thereof, or a pre-cancer condition or disorder, comprising the step of administering to a subject in need thereof a therapeutically effective amount of a salt of formula (I), or any compound covered by such formula, e.g., compounds (II), (III), (1), (1A), (1B), (2), (3) or (4), as described herein.

In other embodiments, the present invention provides a salt of formula (I), or any compound covered by such formula, e.g., compounds (II), (III), (1), (1A), (1B), (2), (3) or (4), as described herein, for use in treating a cancer including metastases thereof, or a pre-cancer condition or disorder.

In some embodiments, the cancer is characterized by a non-solid or a solid tumor or a combination thereof. In other embodiments, the cancer is a hematological cancer.

In some specific embodiments, the cancer is characterized by a non-solid tumor selected from lymphoproliferative disorders including leukemias and lymphomas.

In other specific embodiments, the cancer characterized by a solid tumor is selected from the group consisting of tumors in the central nervous system (CNS), liver cancer, colorectal carcinoma, breast cancer, gastric cancer, pancreatic cancer, bladder carcinoma, cervical carcinoma, head and neck tumors, vulvar cancer and dermatological neoplasms including melanoma, squamous cell carcinoma and basal cell carcinomas.

The salt forms of the present invention may be used to treat any mammal, preferably humans. In other embodiments, the present invention relates to a method of treating an individual who is a candidate for a bone marrow transplantation, comprising the step of pre-treating said individual, prior to the transplantation, with a salt of formula (I), or any compound covered by such formula, e.g., compounds (II), (III), (1), (1A), (1B), (2), (3) or (4), as described herein. In other embodiments, the present invention relates to a salt of formula (I), or any compound covered by such formula, e.g., compounds (II), (III), (1), (1A), (1B), (2), (3) or (4), as described herein, for use in pre-treatment prior to a bone marrow transplantation.

In some embodiments, the cancer can be selected from hematological cancers or non-hematological cancers.

Hematological cancers include leukemias, lymphomas and myelomas, including, but not limited to, myeloid leukemia, lymphocytic leukemia, e.g., acute myeloid leukemia (AML), chronic myeloid leukemia (CML), acute lymphocytic leukemia (ALL), chronic lymphocytic leukemia (CLL), Hodgkin's lymphoma, Non-Hodgkin's lymphoma, multiple myeloma, and Waldenstrom's macroglobulinemia. The hematological cancer can be a relapsed/refractory cancer, or a newly diagnosed cancer.

Non-hematological cancers also known as solid tumors include, but are not limited to, sarcoma, carcinoma, fibrosarcoma, myxosarcoma, liposarcoma, chondrosarcoma, osteogenic sarcoma, chordoma, angiosarcoma, endotheliosarcoma, mesothelioma, Ewing's tumor leiomydsarcoma, rhabdomyosarcoma, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatoma bile duct carcinoma, choriocarcinoma, seminoma, embryonal carcinoma, Wilms' tumor cervical cancer, testicular tumor, lung carcinoma, small cell lung carcinoma, bladder carcinoma, epithelial carcinoma, astrocytoma, Kaposi's sarcoma, and melanoma. Each possibility represents a separate embodiment of the invention.

Non-hematological cancers include cancers of organs, wherein the cancer of an organ includes, but is not limited to, breast cancer, bladder cancer, colon cancer, rectal cancer, endometrial cancer, kidney cancer, lung cancer, cervical cancer, pancreatic cancer, prostate cancer, testicular cancer, thyroid cancer, ovarian cancer, brain cancer including ependymoma, glioma, glioblastoma, medulloblastoma, craneopharyngioma, pinealoma, acustic neuroma, hemangioblastoma, oligodendroglioma, menangioma, neuroblastoma, retinoblastoma, and their metastasis. Each possibility represents a separate embodiment of the invention.

In another aspect, the present invention provides a method of treating a pre-cancer condition or disorder, comprising the step of administering to a subject in need thereof a therapeutically effective amount of a salt of formula (I), or any compound covered by such formula, e.g., compounds (II), (III), (1), (1A), (1B), (2), (3) or (4), as described herein.

In another aspect, the present invention provides a salt of formula (I), or any compound covered by such formula, e.g., compounds (II), (III), (1), (1A), (1B), (2), (3) or (4), as described herein, for use in treating a pre-cancer condition or disorder.

The term pre-cancer disorder or condition includes Myelodysplastic Syndromes (MDS). The term "Myelodysplastic Syndromes" (MDS) refers to a heterogeneous group of hematopoietic pre-malignancies characterized by blood cytopenias, ineffective hematopoiesis and a hypercellular bone marrow. The MDSs are preleukemic conditions in which transformation into acute myeloid leukemia (AML) occurs in approximately 30-40% of cases. Unless allogenic stem cell transplantation can be offered, MDS is generally considered to be an incurable condition.

The present invention further provides a method for the treatment of an infection caused by a viral agent that is a cancer-causing virus comprising the step of administering a salt of formula (I), or any compound covered by such formula, e.g., compounds (II), (III), (1), (1A), (1B), (2), (3) or (4), as described herein. Thus, the invention provides a method for the treatment of a viral infection caused by a viral oncogene. Non-limiting examples of such viruses include human papillomavirus, Hepatitis B, Hepatitis C, Epstein-Barr virus, Human T-lymphotropic virus, Kaposi's sarcoma-associated herpesvirus, and Merkel cell polyomavirus. Each possibility represents a separate embodiment of the invention.

A viral disease can be caused by other viruses including, but not limited to, human immunodeficiency virus (HIV), herpes simplex virus (HSV), cytomegalovirus (CMV), and varicella zoster virus (VZV). Each possibility represents a separate embodiment of the invention. According to one embodiment, the viral disease is Herpes viral encephalitis.

The method of the present invention can be useful for treating a neoplastic disease in a subject having an immunological disease or disorder. Immunological diseases or disorders include, but are not limited to, rheumatoid arthritis (RA), psoriatic arthritis, systemic lupus erythematosus (SLE), lupus nephritis, Inflammatory bowel disease (IBD), irritable bowel syndrome, type I diabetes, immune thrombocytopenic purpura, multiple sclerosis, Sjorgren's syndrome, Hashimoto's thyroiditis, Grave's disease, primary biliary cirrhosis, Wegener's granulomatosis, tuberculosis, and Waldenstrom's macroglobulemia.

The method of the present invention can be useful for treating a neoplastic disease in subjects having organ dysfunction, such as hepatic dysfunction, renal dysfunction, pancreatic dysfunction, bone marrow dysfunction, and cerebellar dysfunction.

The term "hepatic dysfunction" refers to a state in which the liver function is decreased relative to a normal state. In general, hepatic dysfunction is a state characterized in that any one or more measurement values of inspection items for liver function (e.g. levels of blood AST, ALT, ALP, TTT, ZTT, total bilirubin, total protein, albumin, lactate dehydrogenase, choline esterase and the like) are deviated from the range of normal values (reference values). Hepatic dysfunction is characteristic of diseases such as, for example, fulminant hepatitis, chronic hepatitis, viral hepatitis, alcoholic hepatitis, hepatic fibrosis, liver cirrhosis, hepatic cancer, autoimmune hepatitis, drug allergic hepatopathy, and primary biliary cirrhosis.

Renal dysfunction is characteristic of diseases such as, for example, acute renal failure, glomerulonephritis, chronic renal failure, azotemia, uremia, immune renal disease, acute nephritic syndrome, rapidly progressive nephritic syndrome, nephrotic syndrome, Berger's Disease, chronic nephritic/proteinuric syndrome, tubulointerstital disease, nephrotoxic disorders, renal infarction, atheroembolic renal disease, renal cortical necrosis, malignant nephroangiosclerosis, renal vein thrombosis, renal tubular acidosis, renal glucosuria, nephrogenic diabetes insipidus, Bartter's Syndrome, Liddle's Syndrome, polycystic renal disease, interstitial nephritis, acute hemolytic uremic syndrome, medullary cystic disease, medullary sponge kidney, hereditary nephritis, and nail-patella syndrome.

Pancreatic dysfunction is characteristic of diseases such as, for example, diabetes, hyperglycemia, impaired glucose tolerance, and insulin resistance.

Bone marrow dysfunction is characteristic of diseases such as, for example, osteomyelitis, dyshematopoiesis, ion deficiency anemia, pernicious anemia, megaloblastosis, hemolytic anemia, and aplastic anemia.

Cerebellar dysfunction is characteristic of motor and neuro-behavioral disorders such as, for example, hypotonia, dysarthria, dysmetria, dysdiadochokinesia, impaired reflex, and intention tremor.

In one embodiment, the subject is a medically compromised subject who is not amenable to treatment with an anti-cancer agent, e.g., cytarabine. The medically compromised subject may be selected from the group consisting of elderly subjects, subjects having hepatic dysfunction, subjects having renal dysfunction, subjects having pancreatic dysfunction, subjects having bone marrow dysfunction, subjects having cerebellar dysfunction, subjects having immunological disorder, subjects having refractory or relapsed hematological cancer, and any combination thereof.

Toxicity and therapeutic efficacy of the compounds described herein can be determined by standard pharmaceutical procedures in cell cultures or experimental animals, e.g., by determining the IC50 (the concentration which provides 50% inhibition of cell growth) and the MTD (Maximal tolerated dose in tested animals) for a subject compound. The data obtained from cell culture assays and animal studies can be used in formulating a range of dosage for use in human subjects. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 pp. 1).

The amount of active agent used in a composition of the present invention is an amount effective to accomplish the purpose of the particular active agent for the target indication. The amount of an active agent in the compositions is typically a therapeutically, pharmacologically, biologically, or chemically effective amount. However, the amount can be less than that amount when the composition is used in a dosage unit form because the dosage unit form may contain a plurality of compounds or active agents in a single composition or may contain a divided pharmacologically, biologically, therapeutically, or chemically effective amount. The total effective amount can then be administered in cumulative units containing, in total, an effective amount of the active agent.

The salt of the invention can be administered in a daily dose ranging from about 0.3 g/m² to about 10 g/m² of the subject's surface area. According to some embodiments, the salt can be administered at a daily dose ranging from about 0.5 g/m² to about 5 g/m² of the subject's surface area. According to some embodiments, the salt can be administered at a daily dose ranging from about 0.5 g/m² to about 4.5 g/m² of the subject's surface area. According to other embodiments, the salt is administered at a daily dose of about 0.3, 0.5, 0.8, 1, 1.5, 2, 2.3, 2.5, 3, 3.5, 4, 4.5, 5, 6, 7, 8, 9, 10 g/m² of the subject's surface area. Each possibility represents a separate embodiment of the invention.

According to some embodiments, the salt of the invention is administered by intravenous infusion at a daily dose ranging from 0.3 g/m² to 4.5 g/m² of the subject's surface area.

According to some embodiments, the pharmaceutical composition is administered at least once a month. According to additional embodiments, the pharmaceutical composition is administered at least twice a month. According to further embodiments, the pharmaceutical composition is administered at least once a week. According to yet further embodiments, the pharmaceutical composition is administered at least twice a week. According to still further embodiments, the pharmaceutical composition is administered once a day for at least one week. According to further embodiments, the pharmaceutical composition is administered at least once a day for at least one week or until the subject is cured.

According to some embodiments, the pharmaceutical composition is administered once a day for at least 2, 3, 4, 5, 6, 8, 10, 12, or at least 14 consecutive days once a month. Alternatively, the pharmaceutical composition is administered once a day for at least 2, 3, 4, 5, 6, or 12 days twice a month, or further alternatively the pharmaceutical composition is administered every day or twice a week until the patient is cured.

In some embodiments, where the pharmaceutical composition is used for preventing recurrence of cancer, the pharmaceutical composition may be administered regularly for prolonged periods of time according to the clinician's instructions.

In some cases it may be advantageous to administer a large loading dose followed by periodic (e.g., weekly) maintenance doses over the treatment period. The compounds can also be delivered by slow-release delivery systems, pumps, and other known delivery systems for continuous infusion. Dosing regimens may be varied to provide the desired circulating levels of a particular compound based on its pharmacokinetics. Thus, doses are calculated so that the desired circulating level of a therapeutic agent is maintained.

Typically, the effective dose is determined by the activity and efficacy of the compound and the condition of the subject as well as the body weight or surface area of the subject to be treated. The dose and the dosing regimen are also determined by the existence, nature, and extent of any adverse side effects that accompany the administration of the compounds in a particular subject.

According to additional embodiments, the subject being treated is a subject of 50 or more years of age, such as of 60, 70, 75 or more years of age. Each possibility represents a separate embodiment of the invention.

According to further embodiments, the compound of the invention is administered in a daily dosage of at least 2, 3, 5, 10, 15, 20, or at least 30 times greater than the maximal standard of care dose of cytarabine alone. Each possibility represents a separate embodiment of the invention. The following examples are to be considered merely as illustrative and non-limiting in nature. It will be apparent to one skilled in the art to which the present invention pertains that many modifications, permutations, and variations may be made without departing from the scope of the invention.

EXAMPLES

The following abbreviations are used in the Examples:

BOC: t-butyloxycarbonyl

DCC: N,N'-dicyclohexylcarbodiimide

DMF: dimethylformamide

DCM: dichloromethane

DIC: diisopropyl carbodiimide

DIEA: diisopropylethylamine

DMAP: dimethyl aminopyridine

Fmoc: 9-fluorenylmethyloxycarbonyl

HBTU: 2-(1H-benzotriazole-1-yl)-1,1,3,3-tetramethyluronium hexafluorophosphate

HOBt: N-hydroxybenzotriazole

HPLC: High Performance Liquid Chromatography

MS: Mass Spectrometry

NMP: N-methyl 2-pyrrolidone

OtBu: t-butyl ester

TFA: trifluoroacetic acid

Example 1: Synthesis of BOC-Asp(Cytarabine)-OtBu (A)—a Protected Precursor of the Salt Form Asp(Cytarabine).Y (1)

BOC-Asp-OtBu (23.7 g), EDC (15.7 g), HOBT (11.1 g) and Ara-C (20 g) were dissolved in 400 ml DMF, and mixed for 24 hours at room temperature. The mixture was evaporated at 80° C. to receive oily residue. The residue was dissolved in 300 ml Ethyl Acetate and extracted successively with 5% NaHCO₃, 0.1M HCl, 5M NaCl. The mixture was evaporated completely to give solid product of protected precursor BOC-Asp(Cytarabine)-OtBu. The precursor was analyzed by HPLC mixed mode chromatography on primesep 100 at gradient of Acetonitrile/H₂O 0.1% TFA to give pick at retention time of 29.6 minutes. Yield of the product precursor was 80-90%, off-white crystals, HPLC purity ≥95%.

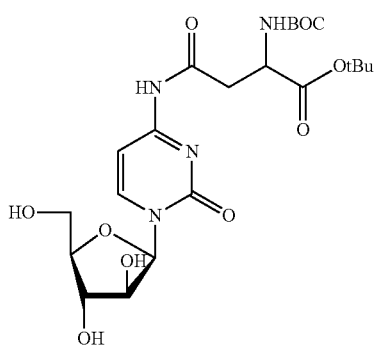

(A)

The protected precursor BOC-Asp(Cytarabine)-OtBu (A) is further used for creation of variety salt forms of the final product Asp(Cytarabine).Y (Y=acid addition salt):

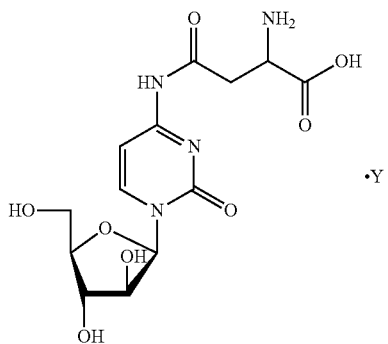

(1)

Example 2: Synthesis of Asp(Cytarabine).Acetate (Y=CH₃COOH), (Formula IV)—Route A Using TFA for Deprotection Protected precursor BOC-Asp(Cytarabine)-OtBu (from example 1) was subjected to cleavage by TFA. Cleavage of the protecting groups (BOC, OtBu) was carried out in 400 ml TFA+2.5% $H_2O$ for 2.5 hours. The solution was transferred to 1.6 L tBME for product precipitation. The precipitate was dried to give off-white crystals of Asp(Cytarabine).TFA, TFA salt form (M.W.=472 g/mol). Asp(Cytarabine).TFA was further dissolved in concentrated acetic acid until complete dissolution. The product was precipitated with tBME and dried to give Asp(Cytarabine).Acetate. Yield of the product was 75-85%, white crystals. The crude product was analyzed by HPLC mixed mode chromatography on primesep 100 at gradient of Acetonitrile/$H_2O$ 0.1% TFA, at 240 nm, to give peak at retention time of 9.2 minutes, purity of 85.3%. MS results show M.W.=359 g/mol (MS+1H). MS results are presented in FIG. 1. Optical density of 213, 245 and 298 nm. NMR results: $^1H$ NMR (600 MHz, DMSO-$_6$d) δ ppm 2.98 (dd, 1H), 3.08 (dd, 1H), 3.61 (d, 1H), 3.84 (ddd, 1H), 3.93 (td, 1H), 4.06 (td, 1H), 4.23 (dtd, 1H),5.50 (s, 1H), 6.05 (d, 1H), 7.12 (d, 1H), 8.09 (d, 1H), 11.10 (s, 1H). $^{13}C$ NMR (151 MHz, DMSO-$_6$d) δ ppm 36.61 (s, 1C), 48.23 (s, 1C), 61.02 (s, 1C), 74.57 (s, 1C), 76.15 (s, 1C), 85.82 (s, 1C), 87.06 (s, 1C), 94.30 (s, 1C), 147.01 (s, 1C), 154.33 (s, 1C), 161.84 (s, 1C), 170.00 (s, 1C), 170.04 (s, 1C). NMR results conforms with the anticipated structure.

Purification of Asp(Cytarabine).Acetate to 95-100% was performed as follows: 7 g of crude product (85.3%) was dissolved in 15 ml $H_2O$ and separated on preparative HPLC as described in Table 1. Solution A—0.1% TFA or 1% Acetic acid dissolved in water. Solution B—0.1% TFA or 1% Acetic acid dissolved in Acetonitrile/Water=9/1. Injection volume: 15 ml, Wavelength: 220 nm, flow rate: 40 ml/min, Column: primesep100, dimension: 60×300 mm, particle size: 10 µm 100A. Fractions collection volume: 30 ml. The collected fractions from minutes 18 to 36 show purity of ≥95% of Asp(Cytarabine).Acetate. The fractions were freeze dried to obtain powder of purified Asp(Cytarabine).Acetate with yield of 3.18 g.

TABLE 1

| Time | A | B |
|---|---|---|
| 0 | 90 | 10 |
| 100 | 90 | 10 |
| 130 | 50 | 50 |
| 160 | 50 | 50 |
| 190 | 90 | 90 |
| 210 | 90 | 90 |

Example 3: Synthesis of Asp(Cytarabine).Methansulfonate by Acid Replacement—Route a Using TFA for Deprotection Two grams of protected precursor BOC-Asp(Cytarabine)-OtBu was subjected to cleavage by TFA as described in example 1. 1 g Asp(Cytarabine).TFA was dissolved in 70% methanesulfonic acid in $H_2O$ to complete dissolution. The product Asp(Cytarabine).methansulfonate was precipitated with isopropanol/tBME and the pellet was dried. Yield of the product was 51%, white crystals. The product was analyzed by HPLC and MS as described in example 2. The product gives peak at retention time of 10.6 minutes, Purity of 80.6%.

Purification of Asp(Cytarabine).methansulfonate to 95-100% was performed accordingly: 20 g of G-10 resin was swelled in 100 ml $H_2O$ for 1 hour. After the swelling G-10 was transferred to sinter glass and washed with 20% ethanol in $H_2O$ (×3 column volumes), $H_2O$, and 0.1% methanesulfonic acid in $H_2O$. One gr Asp(Cytarabine).methanesulfonate crude powder (80.6%) was dissolved with 5 ml $H_2O$. The solution was loaded on G-10 resin and extracted with 0.1% methanesulfonic acid in $H_2O$. Fractions of 5 ml were collected. Purified Asp(Cytarabine).methanesulfonate fractions show purity of over 95%.

Example 4: Synthesis of Asp(Cytarabine).Y Variety of Salt Forms by Acid Replacement Route A can be used for variety of salt forms by replacement of TFA with other acids by the same method as described in examples 2 and 3. Acids such as: benzenesulfonic, benzoic, boric, citric, ethanesulfonic, formic, hydrochloric, lactic, maleic, malonic methanesulfonic, methaphosphoric, nicotinic, oxalic, phosphoric, salicylic, succinic, sulfuric, tartaric, and toluenesulfonic. A variety of acids with selected concentrations and ratio from 1:1 to 1:20 were analyzed for the replacement reactions. After precipitation, the products were analyzed by HPLC and MS. Conditions and results are presented in Table 2. The Asp(Cytarabine).Y products are further purified using purification methods described in examples 2 and 3.

TABLE 2

| Sample of salt form Asp(Cytarabine)•Y | Product:Acid (Y) molar ratio | HPLC Retention Time, minutes | % Product |
|---|---|---|---|
| Asp(Cytarabine)•TFA | 1:1 | 9.50 | 86.49 |
| Asp(Cytarabine)•Acetate | 1:18 | 9.20 | 85.26 |
| Asp(Cytarabine)•hydrochloride | 1:7 | 9.01 | 74.43 |
| Asp(Cytarabine)•Phosphate | 1:16 | 9.13 | 17.36 |
| Asp(Cytarabine)•Citrate | 1:1 | 9.23 | 84.41 |
| Asp(Cytarabine)•Lactate | 1:1.4 | 9.24 | 80.57 |
| Asp(Cytarabine)•Succinate | 1:2 | 9.24 | 73.21 |
| Asp(Cytarabine)•Tartarate | 1:2 | 9.29 | 71.08 |
| Asp(Cytarabine)•Borate | 1:2 | 10.69 | 69.21 |
| Asp(Cytarabine)•Benzoate | 1:2 | 10.63 | 69.48 |
| Asp(Cytarabine)•Benzenesulfonate | 1:2 | 10.62 | 70.73 |
| Asp(Cytarabine)•Ascorbate | 1:2 | 10.64 | 42.1 |
| Asp(Cytarabine)•Methansulfonate | 1:15 | 10.59 | 80.64 |

Figure 2:
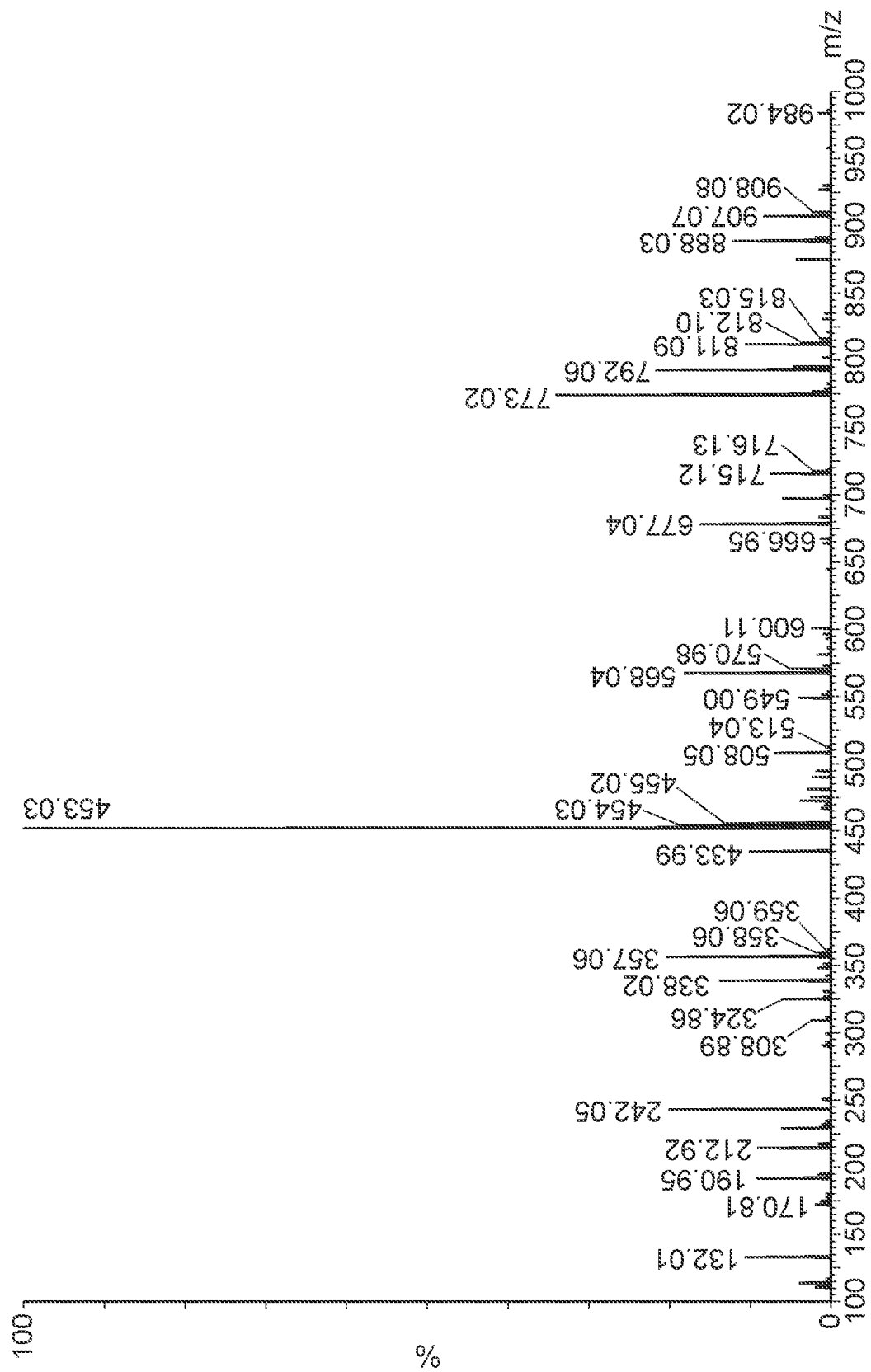
FIG. 2: Mass spectrum of Asp(Cytarabine).methanesulfonate salt (Y=$CH_3SO_3H$).

Example 5: Synthesis of Asp(Cytarabine).Methansulfonate Salt Form by Methanesulfonic Acid Cleavage—Route B 0.25 g of BOC-Asp(Cytarabine)-OtBu precursor (from example 1) was subjected to cleavage by methanesulfonic acid. 0.25 g precursor was added with 1 ml of 70% MSA in $H_2O$ After 2 hr of cleavage the solution was transferred to 10 ml tBME, sediment of the product Asp(Cytarabine).methansulfonate was formed. The product was washed by tBME and dried. Yield of the product was 65%, white crystals. The product was analyzed by HPLC mixed mode chromatography on primesep 100 at gradient of Acetonitril/$H_2O$ 0.1% TFA, at 220 nm, to give peak at retention time of 9.6 minutes, Purity of 56%. MS results of Asp(Cytarabine).methanesulfonate show M.W.=453 and 454 g/mol (MS±1H). MS results are presented in FIG. 2. Asp(Cytarabine).methanesulfonate is purified as described in example 2 and 3. If the purification method in example 2 is used, the acid in use within solutions A and B is replaced to the acid addition salt. Solution A—0.1% methanesulfonic acid dissolved in water. Solution B—0.1% methanesulfonic acid dissolved in Acetonitrile/Water=9/1.

Figure 3:
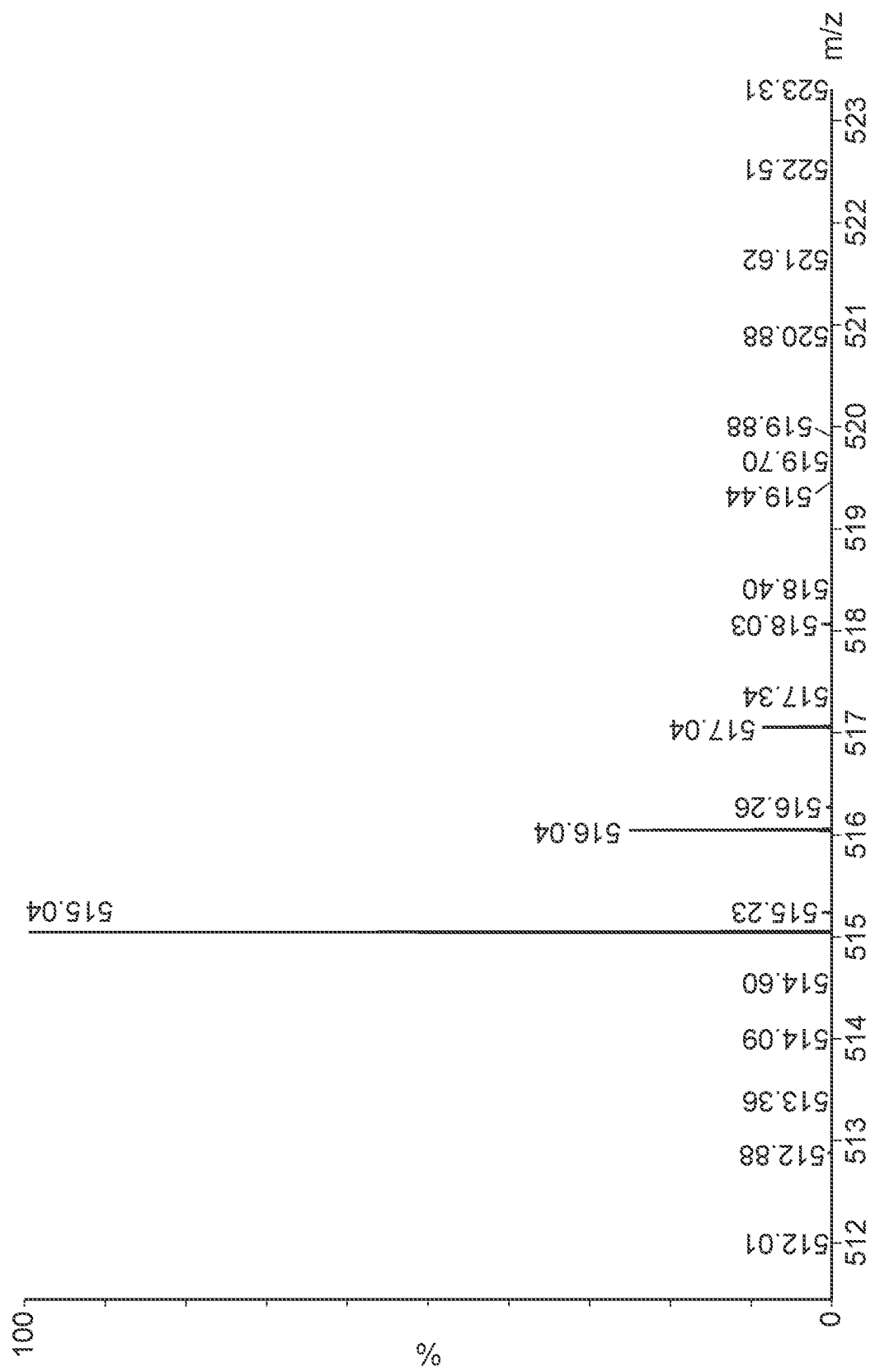
FIG. 3: Mass spectrum of Asp(Cytarabine).benzenesulfonate salt (Y=$C_6H_5SO_3H$).

Example 6: Synthesis of Asp(Cytarabine).Benzenesulfonate Salt Form by Benzenesulfonic Acid Cleavage—Route B Asp(Cytarabine).benzenesulfonate salt form was synthesized from BOC-Asp(Cytarabine)-OtBu precursor by benzenesulfonic acid cleavage as described in example 5. Yield of the product was 31%, white crystals. The product was analyzed as described in example 5. HPLC results show two peaks at retention times of 9.3 and 14.7 minutes, Purity of 20 and 44%, respectively. MS results of Asp(Cytarabine).benzenesulfonate show M.W.=515 and 516 g/mol (MS±1H). MS results are presented in FIG. 3. Asp(Cytarabine).benzenesulfonate is purified as described in example 2, 3 and 5.

Example 7: Synthesis of Asp(Cytarabine).Phosphate Salt Form by Phosphoric Acid Cleavage—Route B Asp(Cytarabine).phosphate salt form was synthesized from BOC-Asp(Cytarabine)-OtBu precursor by concentrated phosphoric acid cleavage as described in example 5. Yield of the product was 34%, white crystals. The product was analyzed as described in example 5. HPLC results show peak at retention times of 9.0 minutes, Purity of 84.3%. MS results of Asp(Cytarabine).phosphate show M.W.=455 and 456 g/mol (MS±1H). Asp(Cytarabine).phosphate is purified as described in example 2, 3 and 5.

Example 8: Synthesis of Asp(Cytarabine).Sulfate Salt Form by Sulfuric Acid Cleavage—Route B Asp(Cytarabine).phosphate salt form was synthesized from BOC-Asp(Cytarabine)-OtBu precursor by concentrated sulfuric acid cleavage as described in example 5. Yield of the product was 77%, white crystals, M.W.=456 g/mol. The product was analyzed as described in example 5. HPLC results show peak at retention times of 9.3 minutes, Purity of 53%. MS results of Asp(Cytarabine).sulfate show M.W.=455 and 456 g/mol (MS±1H). Asp(Cytarabine).sulfate is purified as described in example 2, 3 and 5.

Example 9: Synthesis of Asp(Cytarabine).Hydrochloride Salt Form by Hydrochloric Acid Cleavage—Route C 1 g of BOC-Asp(Cytarabine)-OtBu precursor (from example 1) was subjected to cleavage by HCl. 3 ml of 37% HCl/$H_2O$ was added to the precursor and incubated for 1 hour for the removal of BOC and OtBu protecting groups and salt form formation. The solution was titrated with 1N NaOH to pH=5-6. During the titration white sediment was formed. The received sediment was dried, dissolved in 2 ml $H_2O$ and lyophilized. The product was analyzed as described in example 5. HPLC results show peak at retention times of 9.46 minutes, Purity of 75.9%. Asp(Cytarabine).hydrochloride is purified as described in example 2, 3 and 5.

Example 10: Synthesis of Asp(Cytarabine).Y Variety of Salt Forms by Acid Cleavage Routes B and C can be used for variety of salt forms formation by cleavage with the acid that creates the salt form by the same methods as described in examples 5 and 9. The preferable acids for both removing protecting groups and salt form formation have a pKa≤3, with ratio of 1:1 to 30:1 (acid: precursor). For example acids such as: benzenesulfonic, camphorsulfonic, cyclamic, 2,2-dichloro-acetic, di(t-butyl)-naphthalenesulfonic, di(t-butyl)-naphthalenedisulfonic, dodecylsulfuric, ethane-1,2-disulfonic, ethanesulfonic, fumaric, galactaric, gentisic, glucaric, gluconic, glycerophosphoric, hydrochloric, hydrobromic, hydroiodic, 2-hydroxy-ethanesulfonic (isethionic), 1-hydroxy-2-naphtoic, maleic, malonic, medronic (bisphosphonic), methanesulfonic, methaphosphoric, methylboronic, naphthalene-1,5-disulfonic, naphthalene-2-sulfonic, nitric, orotic, oxalic, 2-oxoglutaric (ketoglutaric), pamoic (embonic), pyruvic, phosphoric, saccharine, salicylic, sulfuric, tartaric, thiocyanic, toluenesulfonic and trifluoroacetic acid, and the like. A variety of acids with selected concentrations from 10% to 100% (concentrated acid) were used for cleavage of BOC-Asp(Cytarabine)-OtBu precursor for protection group removal and salt form formation. The products were further analysed by HPLC and MS. Conditions and results are presented in table 3. Asp(Cytarabine).Y products are purified as described in example 2, 3 and 5.

TABLE 3

| Product | Cleavage acids | Time of cleavage (hr) | HPLC Retention Time (min) | Product (%) |
|---|---|---|---|---|
| Asp(Cytarabine)•TFA salt | TFA/2.5% $H_2O$ | 2.5 | 9.51 | 79.68 |
| Asp(Cytarabine)•hydrochloride | 10% HCl/$H_2O$ | 1 | 9.37 | 18.38 |
| | 37% HCl/$H_2O$ | 1 | 9.46 | 75.94 |
| | | 2 | 9.55 | 75.60 |
| Asp(Cytarabine)•Methansulfonate | Methanesulfonic acid 70% (MSA)/$H_2O$ | 1 | 9.63 | 55.81 |
| | | 2 | 9.5 | 65.51 |
| Asp(Cytarabine)•Benzenesulfonate | Benzenesulfonic acid (BSA)/EA | 1 | 9.23 | 31.55 |
| | | 2 | 9.31 | 20.90 |
| Asp(Cytarabine)•Maleate | Maleic acid/EA | 1 | 8.66 | 27.22 |
| | | 22 | 8.59 | 12.39 |
| Asp(Cytarabine)•Phosphate | Phosphoric acid | 1 | 9 | 84.32 |
| Asp(Cytarabine)•Sulfate | Sulfuric acid | 1 | 9.28 | 77.11 |
| Asp(Cytarabine)•Formate | Formic acid 80%/$H_2O$ | 1 | 9.33 | 0.03 |
| | | 20 | 9.12 | 1.26 |
| Asp(Cytarabine)•Toluensulfonate | P-Toluensulfonic acid/AN | 1 | 9.29 | 0.65 |
| | | 24 | 9.16 | 4.73 |
| Asp(Cytarabine)•Malonate | Malonic acid/AN | 24 | 8.59 | 5.18 |
| Asp(Cytarabine)•Nicotinic salt | Nicotinic acid/EA | 1 | 9.13 | 25.04 |
| | | 24 | 9.03 | 18.72 |
| Asp(Cytarabine)•Oxalate | Oxalic acid/EA | 3 | 4.65 | 96.83 |

Example 11: Preparation of Addition Salt of Asp(Cytarabine).Y with Salts (Such as $NaH_2PO_4$)

BOC-Asp(Cytarabine)-OtBu protected precursor was synthesized as described in example 1. Asp(Cytarabine). TFA was synthesized as described in example 2. 0.25 g of Asp(Cytarabine).TFA was further dissolved in 1 ml of 1M $NaH_2PO_4$ until complete dissolution. The product was precipitated with tBME and dried to give Asp(Cytarabine).phosphate product.

This reaction can be used with other salts such as: $KH_2PO_4$ and the like.

Example 12: Synthesis of BOC-Asp(Gemcitabine)-OtBu (B)—a Protected Precursor of the Salt Form Asp(Gemcitabine).Y (2)

BOC-Asp(Gemcitabine)-OtBu protected precursor was synthesized as described in example 1.

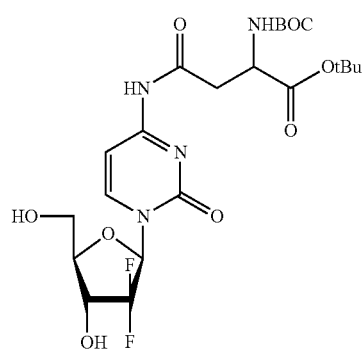

(B)

The protected precursor is further used for creation of variety salt forms of the final product Asp(Gemcitabine).Y (Y=acid addition salt) (2).

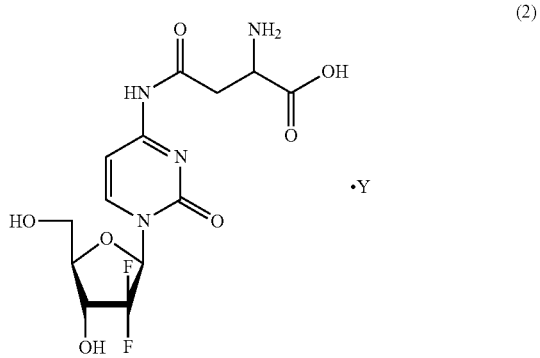

(2)

Example 13: Synthesis of Asp(Gemcitabine).Acetate Salt Form

Asp(Gemcitabine).acetate salt form (Y=$CH_3COOH$) was synthesized from precursor B by acid replacement as described in example 2.

Example 14: Synthesis of Asp(Gemcitabine).Methansulfonate Salt Form

Asp(Gemcitabine).methansulfonate salt form (Y=$CH_3SO_3H$) was synthesized from precursor B by cleavage with methanesulfonic acid as described in example 5.

Example 15: Synthesis of BOC-Glu(Cytarabine)-OtBu (C)—a Protected Precursor of the Salt Form Glu(Cytarabine).Y (3)

BOC-Glu(Cytarabine)-OtBu protected precursor was synthesized as described in example 1.

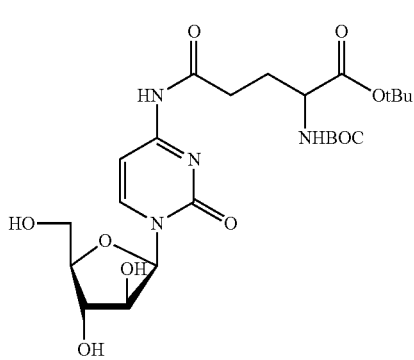

(C)

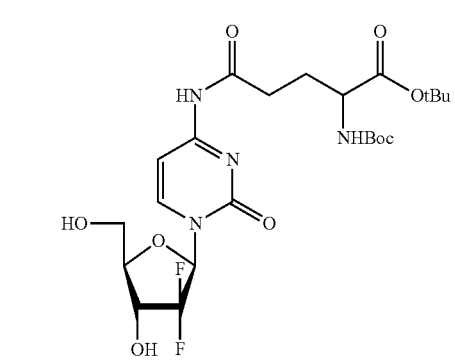

(D)

The protected precursor is further used for creation of variety salt forms of the final product Glu(Cytarabine).Y (Y=acid addition salt) (3).

The protected precursor BOC-Glu(Gemcitabine)-OtBu (D) is further used for creation of variety salt forms of the final product Glu(Gemcitabine) (4).Y (Y=acid addition salt).

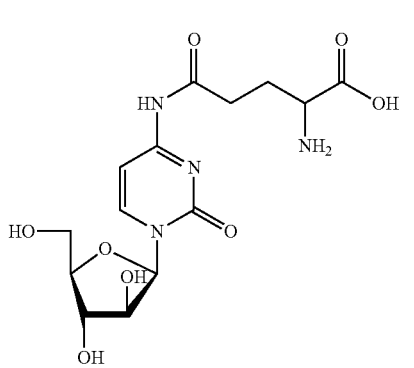

(3)

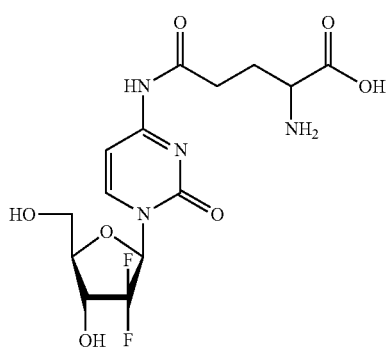

(4)

Example 16: Synthesis of Glu(Cytarabine).Acetate Salt Form

Glu(Cytarabine).acetate salt form (Y=CH$_3$COOH) was synthesized from the precursor C by acid replacement as described in example 2.

Example 17: Synthesis of Glu(Cytarabine).Methansulfonate Salt Form

Glu(Cytarabine).methansulfonate salt form (Y=CH$_3$SO$_3$H) was synthesized from the precursor C by cleavage with methanesulfonic acid as described in example 5.

Example 18: Synthesis of BOC-Glu(Gemcitabine)-OtBu (D)—a Protected Precursor of the Salt Form Glu(Gemcitabine).Y (4)

BOC-Glu(Gemcitabine)-OtBu protected precursor was synthesized as described in example 1.

Example 19: Synthesis of Glu(Gemcitabine).Acetate Salt Form

Glu(Gemcitabine).acetate salt (Y=CH$_3$COOH) form was synthesized from the precursor D by acid replacement as described in example 2.

Example 20: Synthesis of Glu(Gemcitabine).Methansulfonate Salt Form

Glu(Gemcitabine).methansulfonate salt form (Y=CH$_3$SO$_3$H) was synthesized from the precursor D by cleavage with methanesulfonic acid as described in example 5.

Example 21: Synthesis of Asp(Cytarabine).HCl Salt Form (Y=HCl)

Stage 1: Synthesis of Boc-Asp(Cytarabine)-OtBu

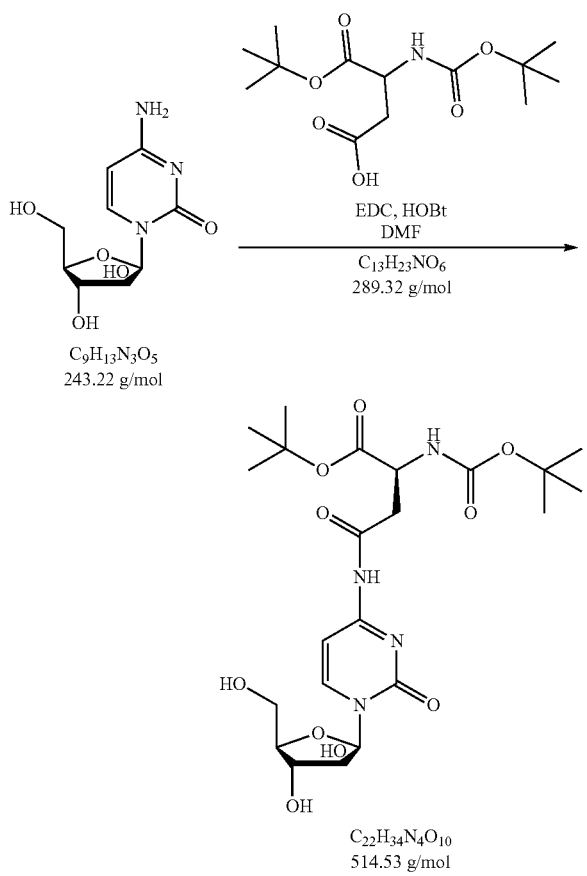

| Isopropanol in ethyl acetate | Column Volumes |
|---|---|
| 5%-10% | 15.0 |
| 10%-20% | 3.0 |
| 20% | 5.0 |

Figure 4:
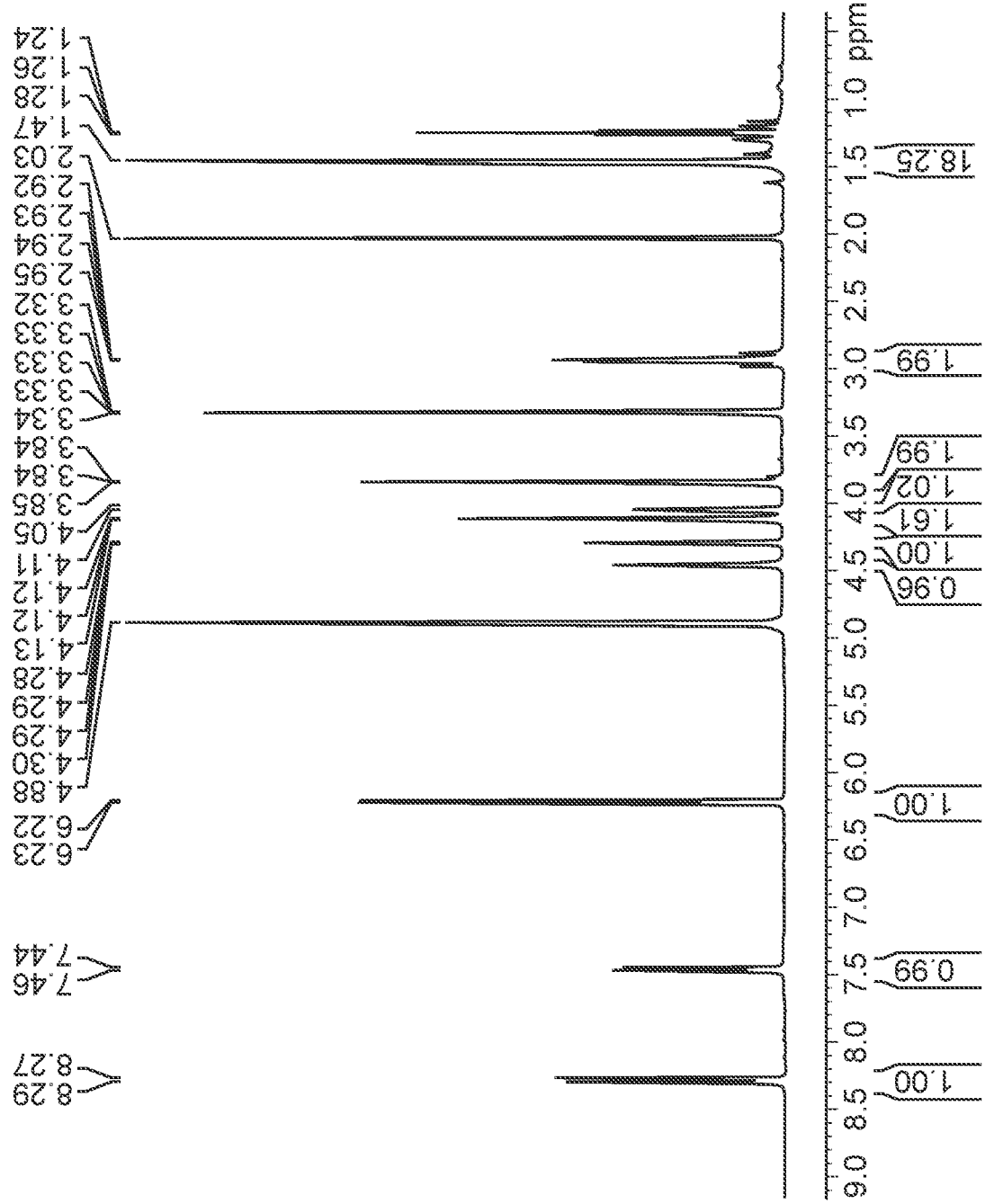
FIG. 4: $^1$H-NMR of purified BOC-Asp-OtBu-(Cytarabine).

The product fractions were combined and evaporated to dryness, yielding 3.78 g of purified product. The $^1$H-NMR spectrum (MeOD) of purified Boc-Asp-OtBu-(Cytarabine) is set forth in FIG. 4.

Stage 3: Synthesis of Asp(Cytarabine).HCl

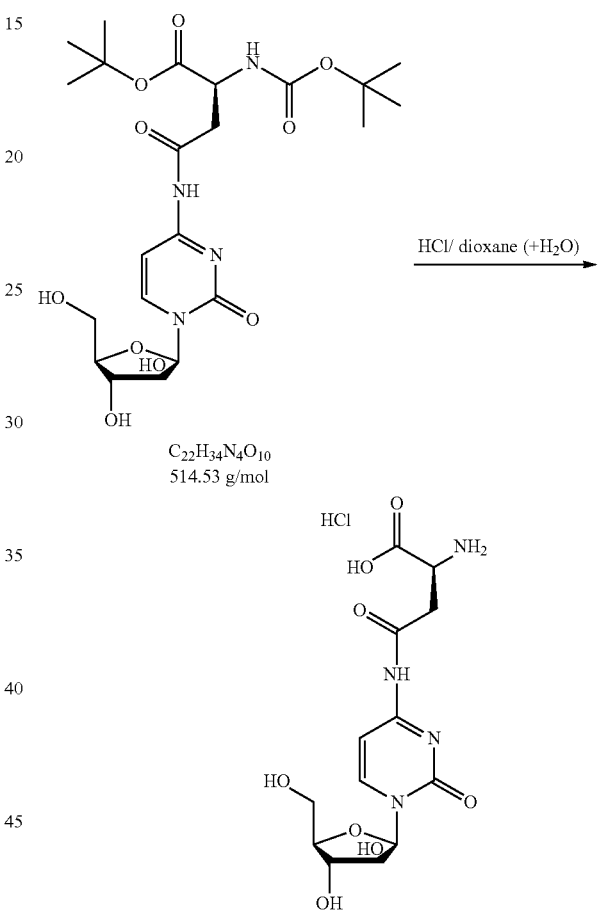

Cytarabine (0.50 g, 2.1 mmol) was suspended in 5 mL dry DMF. The mixture was heated to 70° C. until a clear solution was obtained. Boc-Asp-OtBu (0.40 g, 1.4 mmol) was dissolved at room temperature in 5 mL dry DMF. HOBt (0.22 g, 1.5 mmol) was added and dissolved, followed by EDC (0.28 g, 1.5 mmol). The solution is stirred at room temperature for 30 min.

At 45° C., the activated amino acid was added dropwise to the solution of Cytarabine over 2 h, and then stirred at 45° C. overnight.

The solvent was evaporated under reduced pressure at 60° C. The oily residue was dissolved in ethyl acetate (55 mL) and washed with 3×5% NaHCO$_3$, 3×0.1 M HCl and 3× Brine (15 mL each washing). After drying over sodium sulfate and filtration, the solvent was evaporated and the crude product obtained as foamy solid. The crude product contains ~5-15% (Boc-Asp-OtBu)$_2$-(Cytarabine) impurity.

Stage 2: Purification of Boc-Asp(Cytarabine)-OtBu

The crude product is purified using a Biotage Isolera® purification system. 3.97 g of crude product (contains less than 1% (Boc-Asp-OtBu)$_2$-Cytarabine impurity) were purified using a SNAP Cartridge, KP-SIL 100 g Silica Column with the following gradient at a flow rate of 40 mL/min (Monitoring at 254 nm).

Figure 5:
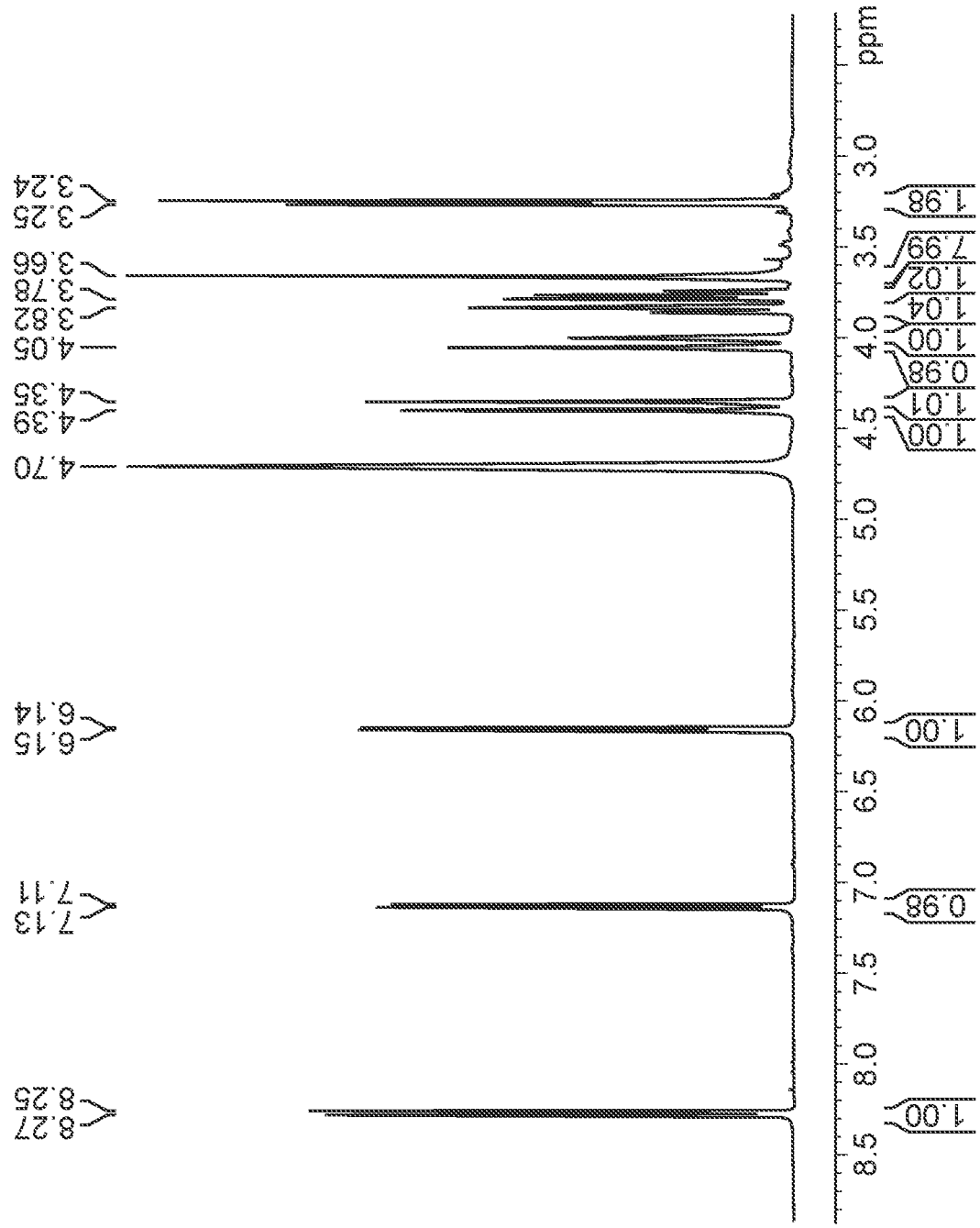
FIG. 5: $^1$H-NMR of Asp(Cytarabine).HCl.

Boc-Asp-OtBu-(Cytarabine) (3.6 g, 7.0 mmol) was dissolved in 8.8 mL dry dioxane. After a clear solution was obtained HCl in dioxane (4 M, 17.5 mL, 70 mmol) was added, at the mixture stirred overnight (after 1 min, a white solid is formed) at room temperature. H$_2$O (0.26 mL, 7.0 mmol) is added dropwise, and stirring continued for 3 hours. The precipitate was filtered (sintered glass filter por. 4) and washed with dry dioxane (2×25 mL). The obtained white solid was dried in vacuum at room temperature to yield in a white powder (3.34 g). The $^1$H-NMR spectrum (MeOD) of Asp(Cytarabine).HCl is set forth in FIG. 5.

Example 22: Synthesis of Asp(Cytarabine).HCl Salt Form (Y=HCl) from Protected Cytarabine Stage 1: Protection of Cytarabine
2.44 g Cytarabine and 1.5 g t-butyldimethylsilyl chloride (TBDMS-Cl) were dissolved in 20 ml pyridine, the reaction was mixed for 10 hours. The solution was evaporated and the pellet was washed with water and ethyl acetate to give white solid of TBDMS-Cytarabine (5'-OH protected).
Stage 2: Synthesis of Boc-Asp(TBDMS-Cytarabine)-OtBu
1 gr TBDMS-Cytarabine was dissolved in 10 mL DMF. 0.8 g Boc-Asp-OtBu was dissolved in 5 mL DMF. 0.44 g HOBt was added and dissolved, followed by 0.56 g EDC. The solution is stirred at room temperature for 30 min. The activated amino acid was added dropwise to the solution of TBDMS-Cytarabine, and then stirred overnight.
The solvent was evaporated under reduced pressure at 60° C. The oily residue was dissolved in ethyl acetate and washed with 5% $NaHCO_3$, 0.1 M HCl and Brine. 2/3 of the solvent was evaporated and the crude product was precipitated by hexane to give white solid. The crude product does not contain $(Boc-Asp-OtBu)_2$-(TBDMS-Cytarabine) impurity, no column purification was needed.
Stage 3: Synthesis of Asp(Cytarabine).HCl
Boc-Asp(TBDMS-Cytarabine)-OtBu was used for synthesis Asp(Cytarabine).HCl using the same process as described in stage 3 of example 22.

Example 23: Biological Activity of Asp(Cytarabine).Y Salt Forms, Effect on Proliferation of Leukemia Cancer Cells The L1210 leukemia cancer cells were grown in DMEM medium with 10% Donor Horse Serum, 1% Glutamine, 1% Non-essential Amino Acids, 0.1% Amphotericin, and 0.1% Gentamicin. Cells were diluted and seeded into 96-wells plate 2000 cells/ml, 400 cells/well, in a volume of 0.2 ml per well. The plates were incubated at 37° C. for 180 min. Following incubation, test substances were added at increasing concentrations from 1 μM to 100 nM formulated in saline in 6 replicates each. The tested substances were Asp(Cytarabine).Acetate salt form, Asp(Cytarabine).hydrochloride salt form, Asp(Cytarabine).Methansulfonate salt form, Asp(Cytarabine).Benzenesulfonate salt form and Asp (Cytarabine).phosphate salt form. Test plates also included 6 replicate wells of saline as control. Plates were incubated at 37° C. for 72 hr prior to analysis. At the end of the exposure period, an MTT [3-(4,5-dimethylthiazole-2-yl)-2,5-diphenyl tetrazolium bromide] assay was performed. To each test well MTT at concentration of 5 mg/ml was added in a volume of 0.02 ml. Plates were incubated at 37° C. for 3 hr, then centrifuged at 3500 rpm for 6 minutes and the supernatants were aspirated. The pellets which contained MTT crystals were dissolved in 0.2 ml DMSO each. Absorbance was determined using ELISA reader at a wavelength of 570 nm. The IC50 values obtained are summarized in Table 4.

TABLE 4

| Test substance salt form | $IC_{50}$ (nM) |
|---|---|
| Asp(Cytarabine)•Acetate salt form | 116 |
| Asp(Cytarabine)•hydrochloride salt form | 240 |
| Asp(Cytarabine)•Benzenesulfonate salt form | 23 |
| Asp(Cytarabine)•phosphate salt form | 34 |
| Asp(Cytarabine)•Methanesulfonate salt form | 2 |

Example 24: Biological Activity of Asp(Cytarabine).Acetate Salt Form, Effect on the Proliferation of Various Cell Lines Variety of Human leukemia cancer cells were grown in RPMI medium with 10% Fetal Bovine Serum, 1% Glutamine, 0.1% Amphotericin, and 0.1% Gentamicin. Cells were diluted and seeded as described in Example 23. Asp(Cytarabine).acetate salt form was added at increasing concentrations from 1 μM to 100 nM formulated in saline in 3 replicates each. MTT assay was performed as described in Example 23. IC50 values obtained are summarized in Table 5.

TABLE 5

| Cell Line | $IC_{50}$ |
|---|---|
| Molt-4, Human acute lymphoblastic leukemia | 12 nM |
| HL-60, Human promyelocytic leukemia | 262 nM |
| CCRF-SB, Human acute lymphoblastic leukemia | 19 μM |
| K562, Human chronic myelogenous leukemia | 355 nM |
| CCRF-CEM, Human acute lymphoblastic leukemia | 23 nM |

It is appreciated by persons skilled in the art that the present invention is not limited by what has been particularly shown and described hereinabove. Rather the scope of the present invention includes both combinations and subcombinations of various features described hereinabove as well as variations and modifications. Therefore, the invention is not to be constructed as restricted to the particularly described embodiments, and the scope and concept of the invention will be more readily understood by references to the claims, which follow.

REFERENCES

Brynes, S, Burckart, G J and Mokotoff, M., 1978a. Potential inhibitors of L-asparagine biosynthesis. 4. Substituted sulfonamide and sulfonylhydrazide analogs of L-asparagine. J Med Chem. 21(1): 45-9.

Brynes S, Fiorina V J, Cooney D A, Milman H A. 1978b. Potential antitumor agents via inhibitors of L-asparagine synthetase: substituted sulfonamides and sulfonyl hydrazides related to glutamine. J Pharm Sci. 67(11): 1550-3.

Dalal M, Plowman J, Breitman T R, et al. 1986. Arabinofuranosyl-5-azacytosine: antitumor and cytotoxic properties. Cancer Res.; 46:831.

Hartel L W, Boder G B, Kroin J S, et al. 1990. Evaluation of the antitumor activity of gemcitabine (2', 2'-difluoro-2'deoxycytidine). Cancer Res.; 50:4417.

Heineman V, Hartel L W, Grindey G B, et al. 1988. Comparison of the cellular pharmacokinetics and toxicology of 2', 2'-difluoro-2' deoxycytidine and 1-13-D-arabinofuranosylcytocsine. Cancer Res 1988; 48:4024.

Ho DHW, 1974. Biochemical studies on new antitumor agent, $O^2$-2'-cyclocyttidine. Biochem Pharmacol.; 23:1235.

Kodama K, Morozumi M, Saitoh K, et al. 1989. Antitumor activity and pharmacology of 1-β-D-arabinofuranosylcytocsine. Jpn J Cancer Res.; 80:679.

Manfredini et al., 2000, Peptide T-araC conjugates: solid phase synthesis and biological activity of N⁴-(Acylpeptidyl)araC, Bioorg. Med. Chem. 8: 539-547.

Piek J, Adelt T, Huse K, Bock W J. [Cerebrospinal fluid and plasma aminogram in patients with primary and secondary tumors of the CNS], [article in German], Infusionsther Klin Ernahr, 1987 April; 14(2): 73-77.

Stammer, C H and Sato, M, 1978. 5-Carboxamido-4-amino-3-isoxazolidone, an asparagine analog, J Med Chem. 21(7):709-712.

Warrell R P Jr, and Berman E, Phase I and II study of fludarabine phosphate in leukemia: efficacy with delayed central nervous system toxicity. J Clin Oncol, 1986 January; 4(1): 74-79.

Woodcock T M, Chou T C, Tan C T C, et al. 1980. Biochemical, pharmacological, and phase I clinical evaluation of pseudoisocytidine. Cancer Res.; 40: 4242.

The invention claimed is:

1. A pharmaceutically acceptable salt represented by the structure of formula (1):

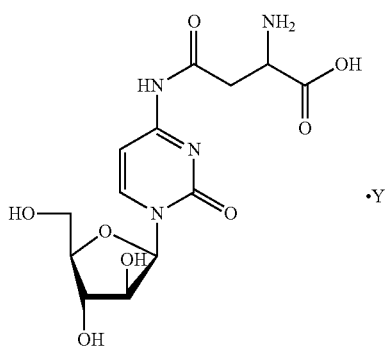

(1)

·Y wherein Y is a pharmaceutically acceptable organic or inorganic acid or a residue thereof, selected from HCl, HBr, methanesulfonic acid, $H_2SO_4$, $H_3PO_4$ or $NaHSO_4$, wherein the pharmaceutically acceptable salt of compound (1) is free of trifluoroacetic acid (TFA).

2. The pharmaceutically acceptable salt according to claim 1, wherein Y is HCl, represented by the structure of:

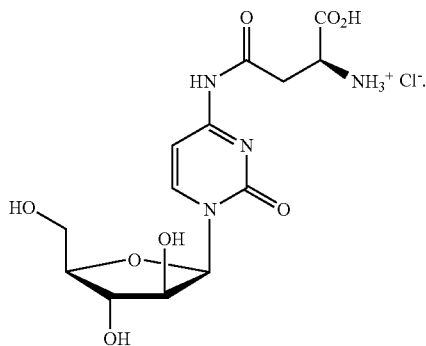

3. The pharmaceutically acceptable salt according to claim 1, wherein Y is methanesulfonic acid, represented by the structure of

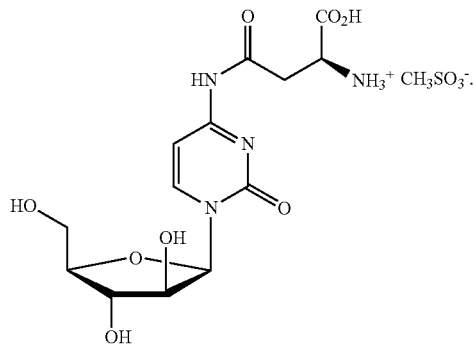

4. The pharmaceutically acceptable salt according to claim 1, wherein Y is $H_2SO_4$, represented by the structure of

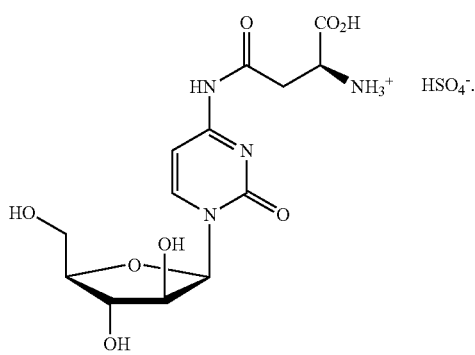

5. The pharmaceutically acceptable salt according to claim 1, wherein Y is $H_3PO_4$, represented by the structure of

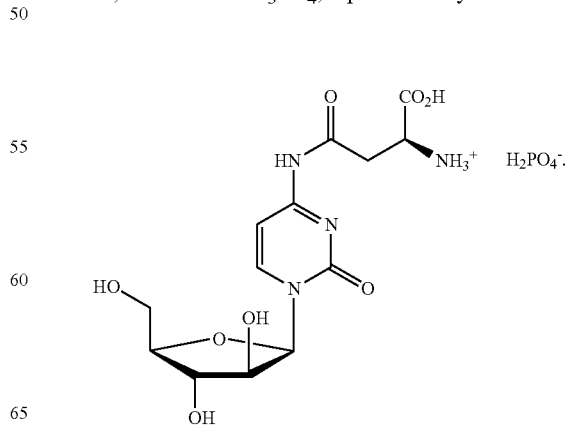

6. The pharmaceutically acceptable salt according to claim 1, wherein the Y is NaHSO₄, represented by the structure of

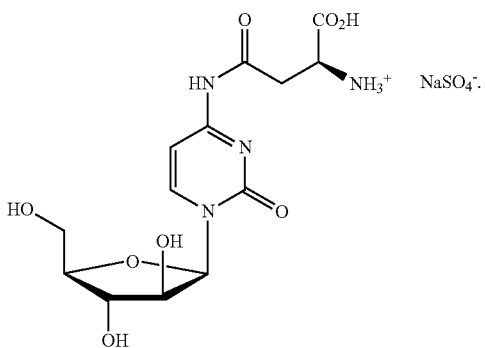

7. A pharmaceutical composition comprising a pharmaceutically acceptable salt according to claim 1 and a pharmaceutically acceptable excipient.

8. A method of treating a cancer or a pre-cancerous condition or disorder comprising administering to a subject in need thereof a therapeutically effective amount of a pharmaceutically acceptable salt according to claim 1.

9. The method of claim 8, wherein the cancer is metastases cancer.

10. The method according to claim 8, wherein the cancer is a non-solid tumor or a solid tumor or a combination thereof.

11. The method according to claim 10, wherein the non-solid tumor comprises leukemias, lymphomas, and multiple myeloma.

12. The method according to claim 11, wherein the leukemia comprises acute myeloid leukemia (AML) and acute lymphoblastic leukemia (ALL).

13. The method according to claim 10, wherein the solid tumor comprises tumors in the central nervous system (CNS), liver cancer, colorectal carcinoma, breast cancer, gastric cancer, pancreatic cancer, bladder carcinoma, cervical carcinoma, head and neck tumors, vulvar cancer, and dermatological neoplasms.

14. The method according to claim 13, wherein the dermatological neoplasms comprise melanoma, squamous cell carcinoma and basal cell carcinomas.

15. The method according to claim 8, wherein the cancer is a hematological cancer.

16. The method of claim 15, wherein the hematological cancer is leukemias, lymphomas and myelomas.

17. The method of claim 16, wherein the cancer is myeloid leukemia, lymphocytic leukemia, acute myeloid leukemia (AMU), chronic myeloid leukemia (CML), acute lymphocytic leukemia (ALL), chronic lymphocytic leukemia (CLL), Hodgkin's lymphoma, Non-Hodgkin's lymphoma, multiple myeloma, or Waldenstrom's macroglobulinemia.

18. The method according to claim 8, wherein the pre-cancer condition or disorder is Myelodysplastic Syndrome (MDS).

19. The method according to claim 8, wherein the subject is a human.

20. A method of treating an individual who is a candidate for a bone marrow transplantation, comprising administering to said individual, prior to the bone marrow transplantation, a pharmaceutically acceptable salt according to claim 1.

21. A method of treating a neoplastic disease in a subject having an immunological disease or disorder, comprising administering a pharmaceutically acceptable salt according to claim 1.

22. A method of treating a neoplastic disease in subjects having organ dysfunction comprising administering to said individual, a pharmaceutically acceptable salt according to claim 1.

* * * * *